US006268473B1

(12) United States Patent
Olivera et al.

(10) Patent No.: US 6,268,473 B1
(45) Date of Patent: Jul. 31, 2001

(54) α-CONOTOXIN PEPTIDES

(75) Inventors: Baldomero M. Olivera, Salt Lake City; Richard T. Layer, Sandy; Maren Watkins, Salt Lake City; David R. Hillyard, Salt Lake City; J. Michael McIntosh, Salt Lake City, all of UT (US); Robert Schoenfeld, Sacramento, CA (US); Robert M. Jones, Salt Lake City, UT (US)

(73) Assignees: University of Utah Research Foundation; Cognetix, Inc., both of Salt Lake City, UT (US)

( * ) Notice: Subject to any disclaimer, the term of this patent is extended or adjusted under 35 U.S.C. 154(b) by 0 days.

(21) Appl. No.: 09/488,799

(22) Filed: Jan. 21, 2000

Related U.S. Application Data
(60) Provisional application No. 60/116,881, filed on Jan. 22, 1999, and provisional application No. 60/116,882, filed on Jan. 22, 1999.

(51) Int. Cl.[7] .............................. C07K 7/08; C07K 14/00; C07K 14/435; A61K 38/10; A61K 38/17
(52) U.S. Cl. ..................... 530/325; 530/325; 530/324; 530/328; 530/350; 435/69.1; 435/69.7; 435/320.1
(58) Field of Search ................... 435/69.7, 69.1, 435/320.1; 530/350, 325, 328

(56) References Cited

U.S. PATENT DOCUMENTS

| 4,447,356 | 5/1984 | Olivera et al. ............ 260/112.5 |
| 5,231,011 | 7/1993 | Hillyard et al. ............. 435/69.7 |
| 5,432,155 | 7/1995 | Olivera et al. .................. 514/12 |
| 5,514,774 | 5/1996 | Olivera et al. ................ 530/324 |
| 5,969,096 | 10/1999 | Shon et al. ................... 530/325 |

FOREIGN PATENT DOCUMENTS

| 0 593 450 | 4/1994 | (EP) . |
| 0 625 162 | 11/1994 | (EP) . |
| WO 91/07980 | 6/1991 | (WO) . |
| WO 93/10145 | 5/1993 | (WO) . |
| WO 93/13128 | 7/1993 | (WO) . |
| WO 99/54350 | 10/1999 | (WO) . |
| WO 00/15654 | 3/2000 | (WO) . |

OTHER PUBLICATIONS

Olivera et al. (1985). *Science* 230:1338–1343.
Olivera et al. (1990). *Science* 249:257–263.
Myers et al. (1993). *Chem. Rev.* 93:1923–1936.
Blount et al. (1992). *Toxicon.* 30(8):835–842.
Gray et al. (1981). *J. Biol. Chem.* 256(10):4734–4740.
Hashimoto et al. (1985). *Eur. J. Pharmacol.* 118:355–354.
Marshall et al. (1990). *Toxicon.* 28(2):231–234.
McManus et al. (1985). *J. Neurosci.* 5(1):110–116.
McManus et al. (1981). *Neurosci. Letts.* 24:57–62.
Smythies (1981). *Medical Hypotheses* 7:1457–1460.
Bevan (1997). *J. Clin. Anesthesia* 9:365, 375, 385, 395.
Bowman (1997). *Asia Pacific J. Pharmacol.* 12:57–64.
Bren et al. (2000). *J. Biol. Chem.*275(17):12692–12700.
Jacobsen et al. (1999). *Biochem.* 38:13310–13315.
Hann et al. (1994). *Biochem.* 33:14058–14063.
Groebe et al. (1997). *Biochem.* 36:6469–6474.
Groebe et al. (1995). *Mol. Pharmacol.* 48:105–111.
Hann et al. (1997). *Biochem.* 36:9051–9056.
Almquist et al. (1989). *Int. J. Peptide Protein Res.* 34:455–462.
McIntosh et al. (1982). *Arch. Biochem. & Biophys.* 218(1):329–334.
Richard M. Hann, et al., "The α–Conotoxins GI and MI Distinguish between the Nicotinic Acetylcholine Receptor Agonist Sites while SI Does Not", Biochemistry vol. 33, No. 47, 1994, pp. 14058–14063.
Duncan R. Groebe, et al., "Determinants Involved in the Affinity of α–Conotoxins GI and SI for the Muscle Subtype of Nicotinic Acetylcholine Receptors", Biochemistry, vol. 36, No. 21, 1997, pp. 6469–6474.
Duncan R. Groebe, et al., "α–Conotoxins Selectively Inhibit One of the Two Acetycholine Binding Sites of Nicotinic Receptors", Molecular Pharmacology, vol. 48, 1995, pp. 105–111.
Ronald G. Almquist, et al., "Paralytic activity of des–Glu[1])conotoxin GI analogs in the mouse diaphragm", Int. J. Peptide Protein Res., vol. 34, 1989, pp. 455–462.
Richard M. Hann, et al., "The 9–Arginine Residue of α–Conotoxin GI is Responsible for Its Selective High Affinity for the αγ Agonist Site on the Electric Organ Acetylcholine Receptor", Biochemistry, vol. 36, No. 29, 1997, pp. 9051–9056.
Richard B. Jacobsen, et al., "Critical Residues Influence the Affinity and Selectivity of α–Conotoxin MI for Nicotinic Acetylcholine Receptors", Biochemistry, vol. 38, No. 40, 1999, pp. 13310–13315.
Nina Bren, et al., "Hydrophobic Pairwise Interactions Stabilize α–Conotoxin Ml in the Muscle Acetylcholine Receptor Binding Site", The Journal of Biological Chemistry, vol. 275, No. 17, Apr. 28, 2000, pp. 12692–12700.
Letter to the Editor, "Development of New Neuromuscular Blocking Drugs", Asia Pacific Journal of Pharmacology, vol. 12, 1997, pp. 57–64.
David R. Bevan, et al. "Neuromuscular Blocking Drugs: Onset and Intubation", Journal of Clinical Anesthesia, vol. 9, Sep. 1997, pp. 383–396.

(List continued on next page.)

Primary Examiner—Karen Cochrane Carlson
Assistant Examiner—Patricia Robinson
(74) Attorney, Agent, or Firm—Rothwell, Figg, Ernst & Manbeck, pc

(57) ABSTRACT

The invention relates to relatively short peptides (termed α-conotoxins herein), about 10–25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants.

33 Claims, 5 Drawing Sheets

OTHER PUBLICATIONS

M. McIntosh, et al., "Isolation and Structure of a Peptide Toxin from the Marin Snal Conus magus", Archives of Biochemistry and Biophysics, vol. 218, No. 1, Oct. 1, 1982, pp. 329–334.

Craig S. Walker, et al., "The T–superfamily of Conotoxins", The Journal of Biological Chemistry, vol. 274, No. 43, Oct. 22, 1999, pp. 30664–30671.

Baldomero M. Olivera, et al., "Generating molecular diversity in Conus venoms", Abstract.

Alan C. Rigby, et al. "A conotoxin from Conus textile with unusual posttranslational modifications reduces presynaptic $Ca^{2+}$influx", Proc. Natl. Acad. Sci. USA, vol. 96, May 1999, pp. 5758–5763.

Internal Scientific Report, Metabolic Stability of CGX–1079 (α–Conopeptide Gl), May 4, 2000.

Alan C. Rigby, et al., "Gamma–carboxyglutamic acid–containing conotoxins in the venom from *Conus textile*", Abstract.

Problem Solving Report Question No.–1026746.044, Neurex—Conotoxin, Calcium Channel Patents, May 2, 2000, Tech.Spec.—John Leavitt.

α-CONOTOXIN PEPTIDES

CROSS-REFERENCE TO RELATED APPLICATIONS

The present application is related to U.S. provisional patent applications Serial Nos. 60/116,881 and 60/116,882, both filed on Jan. 22, 1999 and both incorporated herein by reference.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The invention relates to relatively short peptides (termed α-conotoxins herein), about 10–25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these peptides are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conantokins have been isolated from *Conus geographus* and *Conus tulipa* (Mena et al., 1990; Haack et al., 1990).

The α-conotoxins are small peptides highly specific for neuromuscular junction nicotinic acetylcholine receptors (Gray et al., 1981; Marshall and Harvey, 1990; Blount et al., 1992). The α-conotoxin peptides MI and GI are selective for the α/δ subunit interface of the neuromuscular junction nicotinic receptor over the α/γ subunit interface by >10,000 fold, while the α-conotoxin peptides EI and EIA bind both sites with equal affinity. However, none of these peptides show significant affinity for neuronal nicotinic receptors.

Various compounds having muscle relaxant properties are set forth in U.S. Pat. Nos. 4,190,674; 4,508,715; 4,761,418; 4,701,460; 4,179,507; 4,923,898; 5,015,741; and 5,260,337; as well as in Goodman and Gilman's *The Pharmacological Basis of Therapeutics*, Section II, especially Chapter 11, 7th Ed. (1985) and *Physicians Desk Reference*, 48 Ed., pp. 689, 758, 1362 and 1648 (1994).

Compounds having musculoskeletal relaxing properties include (1) agents acting in the central nervous system which are used to relieve pain associated with muscle contraction (e.g., 5-chlorobenzoxazolinone available as Parafon Forte DSC from McNeil Pharmaceutical), and (2) agents acting in the peripheral nervous system used primarily to induce muscle relaxation and hence reduce muscle contraction during anesthesia. The second group of muscle relaxants is subdivided into two groups: (i) non-depolarizing agents which inhibit the activation of muscle receptors (e.g., metocurarine iodide, d-tubocurarine, tubocurarine chloride, pancuronium, gallamine, diallytoiferine, toxiferine, atracurium besylate which is available as Tracrium from Burroughs-Wellcome Co., and vecuronium bromide which is available as Norcuron from Organon Inc.) and (ii) depolarizing agents which transiently activate muscle receptors and result in their blockade (e.g., decamethonium iodide, and succinylcholine chloride which is available as Anectine from Burroughs-Wellcome Co.). The effects of the depolarizing agents are manifested as fasciculations and flaccid paralysis which are observed to occur rapidly after their injection.

The effects of depolarizing agents (DA) and non-depolarizing agents (NDA) are separated based on their duration of action from ultrashort acting (e.g., for a depolarizing agent such as succinylcholine chloride) to intermediate (e.g., for a non-depolarizing agent such as atracurium besylate). Certain types of muscle relaxants are useful as neuromuscular blocking agents in clinical applications, and have found use as adjuvants to surgical anesthesia, in orthopedic surgical procedures and in facilitating endotracheal intubation procedures. Some of these compounds (e.g., succinylcholine chloride) are routinely used to provide muscle relaxation during Cesarean section procedures.

It is desirable for neuromuscular blocking agents to be locally acting and highly selective for binding to muscle nicotinic acetylcholine receptor sites. As such, when a patient is treated with anesthesia, the muscle relaxant is applied (e.g., intravenously or by injection), in order to cause the muscle to relax and hence minimize muscle contraction.

In anesthesia, neuromuscular blocking agents are used to provide skeletal muscular relaxation during surgery and during intubation of the trachea. All of the conventional nondepolarizing agents when used for producing skeletal muscle relaxation in surgery have a long duration of action e.g., 60 to 180 minutes in man. The depolarizing agents on the other hand provide muscle relaxation at dosages normally used for surgery which is less than the duration of action of nondepolarizing agents. For example, succinylcholine provides a short duration of action of about 5 to 15 minutes whereas decamethonium provides about 20 to 40 minutes duration of muscle relaxation. The long duration of action of nondepolarizing agents is unacceptable in many surgical procedures which take less than one hour because the patient is not generally fully recovered from their effects e.g., the patient may be unable to breathe adequately on his or her own.

Each nondepolarizing agent has inherent side-effects. For example, gallamine and pancuronium may cause tachycardia, d-tubocurarine and diallyltoxiferine may cause hypotension, and succinylcholine may cause fasciculations, myalgia, potassium release, cardiovascular effects, immunological reactions and malignant hyperthermia. While such drugs can be pharmacologically antagonized with anticholinesterase agents, this obviously necessitates the administration of a second drug which itself may have its own side effects e.g., bradycardia, gut spasm and bronchorrhea. Thus to overcome the aforementioned side-effects of the anticholinesterase agents, a third drug, an anticholinergic drug e.g., atropine must also be given.

With the use of depolarizing agents, there is no need to reverse the effects of the depolarizing agents, in certain patients the effects are much prolonged because of abnormal metabolism of the agent by the patient. The polarizing agents due to the mode of action which initially causes skeletal muscle contraction and stimulation of smooth muscles are also known to cause the following side-effects in certain instances; increased intraocular, and intragastric tension, cardiac arrhythmias, potassium release, and muscle pain. These side-effects caused by the depolarizing agents are not caused by the nondepolarizing agents. It is therefore clearly evident that a new neuromuscular blocking agent having the relatively few side-effects and the reversibility of the nondepolarizing agents yet being of considerably shorter i.e., intermediate, duration of action is needed.

It is desired to provide a compound useful as a muscle relaxant. In particular, it is desired to provide an agonist which has activity at relatively low concentrations as a neuromuscular blocking agent. It is also desired to achieve muscle relaxation at concentrations of agonist that are devoid of any ganglionic effects (e.g., so as to not exhibit side effects such as those associated with interaction with cardiovascular sites). As such, it is desired to provide muscle relaxant compositions and methods for providing muscle relaxation. Finally, it is desired to identify additional α-conotoxin peptides for use as neuromuscular blocking agents.

SUMMARY OF THE INVENTION

The invention relates to relatively short peptides (termed α-conotoxins herein), about 10–25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants, for treating benign essential blepharospasm and other forms of focal dystonia and for anti-wrinkle use.

More specifically, the present invention is directed to the neuromuscular blocking use of α-conotoxin peptides of two classes, namely, (a) α3/5 or α3/6 and (b) α4/7, as described herein. The first class of α-conotoxin peptides has the general formula I:

$Xaa_1$-$Xaa_2$-$Xaa_3$-$Xaa_4$-Cys-Cys-$Xaa_5$-$Xaa_6$-$Xaa_7$-Cys-$Xaa_8$-$Xaa_9$-$Xaa_{10}$-$Xaa_{11}$-$Xaa_{12}$-$Xaa_{13}$-Cys-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$ (SEQ ID NO:1), wherein $Xaa_1$ is des-$Xaa_1$ or Gly; $Xaa_2$ is des-$Xaa_2$, Asn, Arg, Asp, Ser, Thr, Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_3$ is des-$Xaa_3$, (Gly, Glu or γ-carboxy-Glu (Gla); $Xaa_4$, is des-$Xaa_4$, Glu, Gla, Gln, pyro-Glu, Arg, Ile Tyr, mono-halo-Tyr, di-halo-Tyr, O-sulpho-Tyr, O-phospho-Tyr, nitro-Tyr, Cys, His, halo-His, any unnatural hydroxy containing amino acid (such as 4-hydroxymethyl-Phe, 4-hydroxyphenyl-Gly, 2,6-dimethyl-Tyr and 5-amino-Tyr), Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_5$ is His, Asn or halo-His; $Xaa_6$ is Pro or hyroxy-Pro; $Xaa_7$ is Ala, Gly, Ser or Thr; $Xaa_8$ is Gly or Ala; $Xaa_9$ is Arg, Lys, Pro, hydroxy-Pro, Gly, Gln, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{10}$ is His, halo-His, Asn, Lys, Tyr, mono-halo-Tyr, di-halo-Tyr, O-sulpho-Tyr, O-phospho-Tyr, nitro-Tyr, N-methy-Lys, N,N-dimethyl-Lys, N,N,N-trimethyl-Lys, Arg, homoarginine, ornithine or any unnatural basic amino acid (such as N-1-(2-pyrazolinyl)-Arg); $Xaa_{11}$ is Tyr, Phe, mono-halo-Tyr, di-halo-Tyr, O-sulpho-Tyr, O-phospho-Tyr, nitro-Tyr, any unnatural hydroxy containing amino acid (such as 4-hydroxymethyl-Phe, 4-hydroxyphenyl-Gly, 2,6-dimethyl-Tyr and 5-amino-Tyr), Trp (D or L), halo-Trp, neo-Trp, or any unnatural aromatic amino acid (such as nitro-Phe, 4-substituted-Phe wherein the substituent is $C_1$–$C_3$ alkyl, carboxyl, hyrdroxymethyl, sulphomethyl, halo, phenyl, —CHO, —CN, —$SO_3H$ and —NHAc); $Xaa_{12}$ is Ile, Ser, Thr, Asp, Gly, Asn, Glu, Gla or Val; $Xaa_{13}$ is des-$Xaa_{13}$, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{14}$ is des-$Xaa_{14}$, Gly, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{15}$ is des-$Xaa_{15}$, Gly, Thr, Ser, His, halo-His, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{16}$ is des-$Xaa_{16}$, Ser or Thr; $Xaa_{17}$ is des-$Xaa_{17}$ or Cys; $Xaa_{18}$ is des-$Xaa_{18}$, Ser or Thr; $Xaa_{19}$ is des-$Xaa_{19}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{20}$ is des-$Xaa_{20}$, Thr, Ser, Pro or hydroxy-Pro; $Xaa_{21}$, is des-$Xaa_{21}$, Leu, Ser or Thr; $Xaa_{22}$ is des-$Xaa_{22}$, Glu or Gla; $Xaa_{23}$ is des-$Xaa_{23}$, Pro or hydroxy-Pro; $Xaa_{24}$ is des-$Xaa_{24}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg); and $Xaa_{25}$ is des-$Xaa_{25}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg). The C-terminus may contain a free carboxyl group or an amide group, preferably an amide group. The halo is chlorine, bromine or iodine, preferably iodine for Tyr and bromine for Trp. The Cys residues may be in D or L configuration and may optionally be substituted with homocysteine.

Useful peptides include GI (Gray et al., 1981), GIA (Gray et al., 1981), GII (Gray et al., 1981), MI (McIntosh et al., 1982), SI (Zafaralla et al., 1988), SIA (Myers et al., 1991), SIB (same as SI, except further contains Glu at N-terminus), SII (Olivera et al., 1996), SIIA (Olivera et al., 1996), RI (same as G1, except Tyr for Lys), R1.3 (below), R1.4 (below), Sm1.1 (below), S11 (below), S2 (below); GIB (same as R1); MnII (below); A1.2 (below); A1.3 (below); A1.7 (below); A1.8 (below); Ay1.1 (below); Ay1.1a (below); M1.1 (below); M1.3 (below); M1.4 (below); M1.5 (below); O1.3 (below); S1.3 (below); Sa (below).

The second class of α-conotoxin peptides has the general formula II:

$Xaa_1$-$Xaa_2$-$Xaa_3$-Cys-Cys-$Xaa_4$-$Xaa_5$-$Xaa_6$-$Xaa_7$-Cys-$Xaa_8$-$Xaa_9$-$Xaa_{10}$-$Xaa_{11}$-$Xaa_6$-$Xaa_{12}$-Ile-Cys-$Xaa_{13}$-$Xaa_{14}$-$Xaa_{15}$ (SEQ ID NO:2), wherein $Xaa_1$ is des-$Xaa_1$, Arg, Ser, Thr, Lys, omithine, homoargine, N-methy-Lys, N,N-dimethyl-Lys, N,N,N-trimethyl-Lys or any unnatural basic amino acid (such as N-1-(2-pyrazolinyl)-Arg); $Xaa_2$ is des-$Xaa_2$, Asp, Gly, Leu, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_3$ is des-$Xaa_3$, Pro, hydroxy-Pro, Ala, Gly or Leu; $Xaa_4$ is Tyr, Ser, Thr, mono-halo-Tyr, di-halo-Tyr, O-sulpho-Tyr, O-phospho-Tyr, nitro-Tyr or any unnatural hydroxy containing amino acid (such as 4-hydroxymethyl-Phe, 4-hydroxyphenyl-Gly, 2,6-dimethyl-Tyr and 5-amino-Tyr); $Xaa_5$ is His, Asn, Ile, Tyr, halo-His, mono-halo-Tyr, di-halo-Tyr, O-sulpho-Tyr, O-phospho-Tyr or nitro-Tyr; $Xaa_6$ is Pro or hydroxy-Pro; $Xaa_7$ is Thr, Ala, Val, Ser, Pro or hydroxy-Pro; $Xaa_8$ is Asn, Thr, Ser, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_9$ is Met, Val, Ala, Leu or Ile; $Xaa_{10}$ is Ser, Thr, Asn, His or halo-His; $Xaa_{11}$ is Asn, Tyr, mono-halo-Tyr, di-halo-Tyr, O-sulpho-Tyr, O-phospho-Tyr, nitro-Tyr, or any unnatural hydroxy containing amino acid (such as 4-hydroxymethyl-Phe, 4-hydroxyphenyl-Gly, 2,6-dimethyl-Tyr and 5-amino-Tyr); $Xaa_{12}$ is Glu, γ-carboxy-Glu (Gla), Gln or Asp; $Xaa_{13}$ is des-$Xaa_{13}$ or Gly; $Xaa_{14}$ is des-$Xaa_{14}$ or Gly; and $Xaa_{15}$ is des-$Xaa_{15}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg). The C-terminus may contain a free carboxyl group or an amide group, preferably an amide group. The halo is preferably chlorine or iodine, more preferably iodine. The Cys residues may be in D or L configuration and may optionally be substituted with homocysteine.

Useful peptides include E1 (U007; Olivera et al., 1996), EIA (U008; Olivera et al., 1996), P1.2 (below), P1.3 (below), Sl1.4 (below), Sl1.4A (below); Sl1.8 (below) and Ta (below).

The present invention is also directed to novel specific α-conotoxin peptides of class I having the formulas:

$Xaa_1$-Cys-Cys-Asn-$Xaa_2$-Ala-Cys-Gly-Arg-His-$Xaa_3$-Ser-Cys-$Xaa_4$-Gly (SEQ ID NO:3);

Asn-Gly-Arg-Cys-Cys-His-$Xaa_2$-Ala-Cys-Gly-$Xaa_4$-His-Phe-Ser-Cys (SEQ ID NO:4);

Gly-Arg-Gly-Arg-Cys-Cys-His-$Xaa_2$-Ala-Cys-Gly-$Xaa_2$-Asn-$Xaa_3$-Ser-Cys (SEQ IDNO:5);

Cys-Cys-His-$Xaa_2$-Ala-Cys-Gly-Arg-$Xaa_4$-$Xaa_3$-Asn-Cys (SEQ ID NO:6);

Cys-Cys-Cys-Asn-$Xaa_2$-Ala-Cys-Gly-$Xaa_2$-Asn-$Xaa_3$-Gly-Cys-Gly-Thr-Ser-Cys-Ser-Arg-$Xaa_2$-Ser-$Xaa_1$-$Xaa_2$-Arg-Arg (SEQ ID NO:7);

Asn-Gly-His-Cys-Cys-His-$Xaa_2$-Ala-Cys-Gly-Gly-$Xaa_4$-$Xaa_3$-Val-$Xaa_4$-Cys (SEQ ID NO:8);

Asn-Gly-Arg-Cys-Cys-His-$Xaa_2$-Ala-Cys-Gly-Gly-$Xaa_4$-$Xaa_3$-Val-$Xaa_4$-Cys (SEQ ID NO:9);

Asn-Gly-Arg-Cys-Cys-His-$Xaa_2$-Ala-Cys-Gly-$Xaa_4$-His-Phe-Ile-Cys (SEQ ID NO:10);

Asn-Gly-Arg-Cys-Cys-His-$Xaa_2$-Ala-Cys-Gly-$Xaa_4$-His-Phe-Ser-Cys (SEQ ID NO:11);

Asn-Gly-Arg-Cys-Cys-His-$Xaa_2$-Ser-Cys-Gly-Arg-$Xaa_4$-$Xaa_3$-Asn-Cys (SEQ ID NO:12);

Asn-Gly-Arg-Cys-Cys-His-$Xaa_2$-Ala-Cys-Ala-Arg-$Xaa_4$-$Xaa_3$-Asn-Cys (SEQ ID NO:13);

Asn-$Xaa_1$-Arg-Cys-Cys-His-$Xaa_2$-Ala-Cys-Ala-Arg-$Xaa_4$-$Xaa_3$-Asn-Cys (SEQ ID NO:14);

Asp-Gly-Arg-Cys-Cys-His-$Xaa_2$-Ala-Cys-Gly-Gln-Asn-$Xaa_3$-Ser-Cys (SEQ ID NO:15);

Asp-Gly-Arg-Cys-Cys-His-$Xaa_2$-Ala-Cys-Ala-$Xaa_4$-His-Phe-Asn-Cys (SEQ ID NO:16);

Asn-Gly-Arg-Cys-Cys-His-$Xaa_2$-Ala-Cys-Ala-$Xaa_4$-Asn-$Xaa_3$-Ser-Cys (SEQ ID NO:17);

Asn-Gly-Arg-Cys-Cys-His-$Xaa_2$-Ala-Cys-Ala-Arg-$Xaa_4$-$Xaa_3$-Ser-Cys (SEQ ID NO:18);

$Xaa_5$-Cys-Cys-Asn-$Xaa_2$-Ala-Cys-Gly-$Xaa_2$-$Xaa_4$-$Xaa_3$-Ser-Cys (SEQ ID NO:19);

$Xaa_5$-Cys-Cys-His-$Xaa_2$-Ala-Cys-Gly-$Xaa_4$-$Xaa_4$-$Xaa_3$-Asn-Cys (SEQ ID NO:20); and Ser-Gly-Arg-Cys-Cys-His-$Xaa_2$-Ala-Cys-Gly-Arg-$Xaa_4$-$Xaa_3$-Asn-Cys (SEQ ID NO:21), wherein $Xaa_1$ is Glu or γ-carboxy-glutamate (Gla); $Xaa_2$ is Pro or hydroxy-Pro; $Xaa_3$ is Tyr, mono-halo-Tyr, di-halo-Tyr, O-sulpho-Tyr, O-phospho-Tyr or nitro-Tyr; $Xaa_4$ is Lys, N-methyl-Lys, N,N-dimethyl-Lys or N,N,N-trimethyl-Lys; $Xaa_5$ is Gln or pyro-Glu; and the C-terminus contains a carboxyl or amide group, preferably an amide group. The halo is preferably chlorine or iodine, more preferably iodine. In addition, the His residues may be substituted with halo-His; the Arg residues may be substituted by Lys, ornithine, homoargine, N-methy-Lys, N,N-dimethyl-Lys, N,N,N-trimethyl-Lys or any unnatural basic amino acid (such as N-1-(2-pyrazolinyl)-Arg); the Lys residues may be substituted by Arg, omithine, homoargine, N-methy-Lys, N,N-dimethyl-Lys, N,N,N-trimethyl-Lys or any unnatural basic amino acid (such as N-1-(2-pyrazolinyl)-Arg); the Tyr residues may be substituted with any unnatural hydroxy containing amino acid (such as 4-hydroxymethyl-Phe, 4-hydroxyphenyl-Gly, 2,6-dimethyl-Tyr and 5-amino-Tyr); the Ser residues may be substituted with Thr; the Thr residues may be substituted with Ser; and the Phe residues may be substituted with any unnatural aromatic amino acid (such as nitro-Phe, 4-substituted-Phe wherein the substituent is $C_1$–$C_3$ alkyl, carboxyl, hyrdroxymethyl, sulphomethyl, halo, phenyl, —CHO, —CN, —$SO_3H$ and —NHAc).

More specifically, the present invention is directed to the following α-conotoxin peptides of class I:

R1.3: SEQ ID NO:3, wherein $Xaa_1$ is Glu, $Xaa_2$ is Pro, $Xaa_3$ is Tyr and $Xaa_4$ is Lys;

R1.4: SEQ ID NO:4, wherein $Xaa_2$ is Pro and $Xaa_4$ is Lys;

Sm1.1: SEQ ID NO:5, wherein $Xaa_2$ is Pro and $Xaa_3$ is Tyr;

S11: SEQ ID NO:6, wherein $Xaa_2$ is Pro, $Xaa_3$ is Tyr and $Xaa_4$ is Lys;

S2: SEQ ID NO:7, wherein $Xaa_1$ is Glu, $Xaa_2$ is Pro and $Xaa_3$ is Tyr;

MnII: SEQ ID NO:8, wherein $Xaa_2$ is Pro, $Xaa_3$ is Tyr and $Xaa_4$ is Lys;

A1.2: SEQ ID NO:9, wherein $Xaa_2$ is Pro, $Xaa_3$ is Tyr and $Xaa_4$ is Lys;

A1.3: SEQ ID NO:10, wherein $Xaa_2$ is Pro and $Xaa_4$ is Lys;

A1.7: SEQ ID NO:11, wherein $Xaa_2$ is Pro and $Xaa_4$ is Lys;

A1.8: SEQ ID NO:12, wherein $Xaa_2$ is Pro and $Xaa_4$ is Lys;

Ay1.1: SEQ ID NO:13, wherein $Xaa_2$ is Pro, $Xaa_3$ is Tyr and $Xaa_4$ is Lys;

Ay1.1a: SEQ ID NO:14, wherein $Xaa_1$ is Glu, $Xaa_2$ is Pro, $Xaa_3$ is Tyr and $Xaa_4$ is Lys;

M1.1: SEQ ID NO:15, wherein $Xaa_2$ is Pro and $Xaa_3$ is Tyr;

M1.3: SEQ ID NO:16, wherein $Xaa_2$ is Pro and $Xaa_4$ is Lys;

M1.4: SEQ ID NO:17, wherein $Xaa_2$ is Pro, $Xaa_3$ is Tyr and $Xaa_4$ is Lys;

M1.5: SEQ ID NO:18, wherein $Xaa_2$ is Pro, $Xaa_3$ is Tyr and $Xaa_4$ is Lys;

O1.3: SEQ ID NO:19, wherein $Xaa_2$ is Pro, $Xaa_3$ is Tyr, $Xaa_4$ is Lys and $Xaa_5$ is Gln;

S1.3: SEQ ID NO:20, wherein $Xaa_2$ is Pro, $Xaa_3$ is Tyr, $Xaa_4$ is Lys and $Xaa_5$ is Gln; and Sa: SEQ ID NO:21, wherein $Xaa_2$ is Pro, $Xaa_3$ is Tyr and $Xaa_4$ is Lys.

The C-terminus is preferably amidated in each of these specific peptides.

The present invention is also directed to novel specific α-conotoxin peptides of class II having the formulas:

Arg-Asp-$Xaa_2$-Cys-Cys-Ser-Asn-$Xaa_2$-Val-Cys-Thr-Val-His-Asn-$Xaa_2$-Gln-Ile-Cys (SEQ ID NO:22);

Arg-Ala-Cys-Cys-Ser-$Xaa_3$-$Xaa_2$-$Xaa_2$-Cys-Asn-Val-Asn-$Xaa_3$-$Xaa_2$-$Xaa_1$-Ile-Cys (SEQ ID NO:23);

Gly-Gly-Cys-Cys-Ser-$Xaa_3$-$Xaa_2$-$Xaa_2$-Cys-Asn-Val-Ser-$Xaa_3$-$Xaa_2$-$Xaa_1$-Ile-Cys (SEQ ID NO:24);

Cys-Cys-Ser-$Xaa_3$-$Xaa_2$-$Xaa_2$-Cys-Asn-Val-Ser-$Xaa_3$-$Xaa_2$-$Xaa_1$-Ile-Cys (SEQ ID NO:25);

Ala-Cys-Cys-Ser-$Xaa_3$-$Xaa_2$-$Xaa_2$-Cys-Asn-Val-Asn-$Xaa_3$-$Xaa_2$-$Xaa_1$-Ile-Cys-Gly-Gly-Arg (SEQ ID NO:26); and Ser-Leu-Leu-Cys-Cys-Thr-Ile-$Xaa_2$-Ser-Cys-$Xaa_4$-Ala-Ser-$Xaa_3$-$Xaa_2$-Asp-Ile-Cys (SEQ ID NO:27), wherein $Xaa_1$ is Glu or γ-carboxy-Glu (Gla); $Xaa_2$ is Pro or hydroxy-Pro; $Xaa_3$ is Tyr, mono-halo-Tyr, di-halo-Tyr, O-sulpho-Tyr, O-phospho-Tyr or nitro-Tyr; $Xaa_4$ is Lys, N-methyl-Lys, N,N-dimethyl-Lys or N,N,N-trimethyl-Lys; and the C-terminus contains a carboxyl or amide group, preferably an amide group. The halo is preferably chlorine or iodine, more preferably iodine. In addition, the His residues may be substituted with halo-His; the Arg residues may be substituted by Lys, ornithine, homoargine, N-methy-Lys, N,N-dimethyl-Lys, N,N,N-trimethyl-Lys or any unnatural basic amino acid (such as N-1-(2-pyrazolinyl)-Arg); the Lys residues may be substituted by Arg, ornithine, homoargine, N-methy-Lys, N,N-dimethyl-Lys, N,N,N-trimethyl-Lys or any unnatural basic amino acid (such as N-1-(2-pyrazolinyl)-Arg); and the Tyr residues may be substituted with any unnatural hydroxy containing amino acid (such as 4-hydroxymethyl-Phe, 4-hydroxyphenyl-Gly, 2,6-dimethyl-Tyr and 5-amino-Tyr).

More specifically, the present invention is directed to the following α-conotoxin peptides of class II:

P1.2: SEQ ID NO:22, wherein $Xaa_2$ is Pro;

P1.3: SEQ ID NO:23, wherein $Xaa_1$ is Glu, $Xaa_2$ is Pro and $Xaa_3$ is Tyr;

Sl1.4: SEQ ID NO:24, wherein $Xaa_1$ is Glu, $Xaa_2$ is Pro and $Xaa_3$ is Tyr;

Sl1.4A: SEQ ID NO:25, wherein $Xaa_1$ is Glu, $Xaa_2$ is Pro and $Xaa_3$ is Tyr;

Sl1.8: SEQ ID NO:26, wherein $Xaa_1$ is Glu, $Xaa_2$ is Pro and $Xaa_3$ is Tyr; and Ta: SEQ ID NO:27, wherein $Xaa_2$ is Pro, $Xaa_3$ is Tyr and $Xaa_4$ is Lys.

The C-terminus is preferably amidated in each of these specific peptides.

The above and other unnatural basic amino acids, unnatural hydroxy containing amino acids or unnatural aromatic amino acids are described in Building Block Index, Version 3.0 (1999 Catalog, pages 4–47 for hydroxy containing amino acids and aromatic amino acids and pages 66–87 for basic amino acids; see also http://www.amino-acids.com), incorporated herein by reference, by and available from RSP Amino Acid Analogues, Inc., Worcester, Mass.

Optionally, in the peptides of general formulas I and II and the specific peptides described above, the Asn residues may be modified to contain an N-glycan and the Ser and Thr residues may be modified to contain an O-glycan. In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and coinectivities) are defined for each core glycan. Suitable glycans and glycan analogs are described further in U.S. Ser. No. 09/420,797, filed Oct. 19, 1999 and in PCT Application No. PCT/US99/24380, filed Oct. 19, 1999, both incorporated herein by reference. A preferred glycan is Gal(β1→3)GalNAc(α1→).

Optionally, in the peptides of general formulas I and II and the specific peptides described above, pairs of Cys residues may be replaced pairwise with Lys-Glu pairs. Sequential coupling by known methods (Bamay et al., 2000; Hruby et al., 1994; Bitan et al., 1997) allows replacement of native cys bridges with lactam bridges.

The present invention is further directed to propeptides and nucleic acid sequences encoding the propeptides or peptides as described in further detail herein.

SUMMARY OF THE SEQUENCE LISTING

Figure 1:
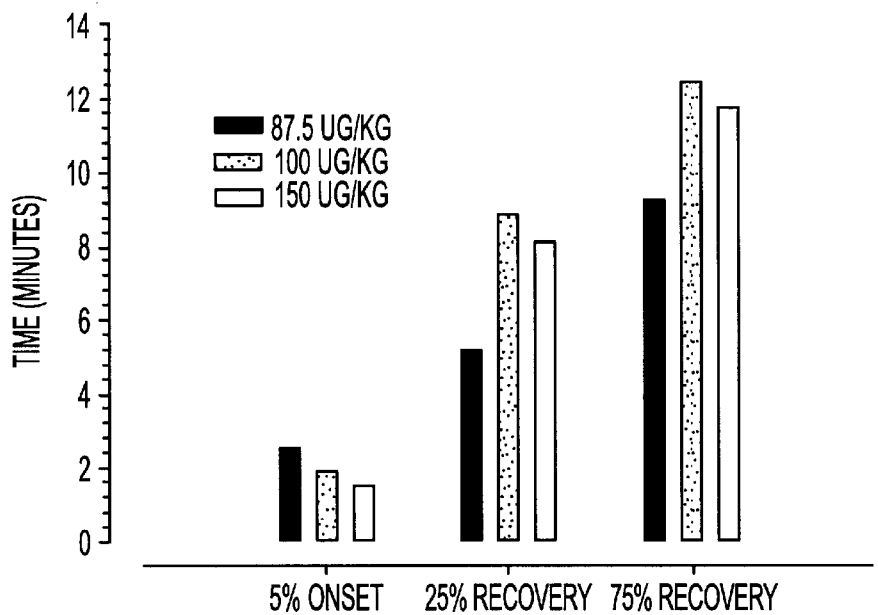
FIG. 1 shows onset and recovery time of neuromuscular block for different doses (87, 100 or 150 μg/kg) of the α-conotoxin peptide MI.

SEQ ID NO:1 is a generic formula for α-conotoxin peptides of Class I useful as neuromuscular blocking agents. SEQ ID NO:2 is a generic formula for α-conotoxin peptides of Class II useful as neuromuscular blocking agents. SEQ ID NO:3 is a generic formula for the peptide R1.3. SEQ ID NO:4 is a generic formula for the peptide R1.4. SEQ ID NO:5 is a generic formula for the peptide Sm1.1. SEQ ID NO:6 is a generic formula for the peptide S11. SEQ ID NO:7 is a generic formula for the peptide S2. SEQ ID NO:8 is a generic formula for the peptide MnII. SEQ ID NO:9 is a generic formula for the peptide A1.2. SEQ ID NO:10is a generic formula for the peptide A1.3. SEQ ID NO:11 is ageneric formula forthe peptide A1.7. SEQ ID NO:12 is a generic formula for the peptide A1.8. SEQ ID NO:13 is a generic formula for the peptide Ay 1.1. SEQ ID NO:14 is a generic formula for the peptide Ay1.1a. SEQ ID NO:15 is a generic formula for the peptide M1.1. SEQ ID NO:16 is a generic formula for the peptide M1.3. SEQ ID NO:17 is a generic formula for the peptide M1.4. SEQ ID NO:18 is a generic formula for the peptide M1.5. SEQ ID NO:19 is a generic formula for the peptide O1.3. SEQ ID NO:20 is a generic formula for the peptide S1.3. SEQ ID NO:21 is a generic formula for the peptide Sa. SEQ ID NO:22 is a generic sequence for the peptide P1.2. SEQ ID NO:23 is a generic sequence for the peptide P1.3. SEQ ID NO:24 is a generic sequence for the peptide S11.4. SEQ ID NO:25 is a generic sequence for the peptide Sl1.4A. SEQ ID NO:26 is a generic sequence for the peptide Sl1.8. SEQ ID NO:27 is a generic formula for the peptide Ta. SEQ ID NO:28 is a DNA sequence coding for the GI propeptide. SEQ ID NO:29 is the amino acid sequence of the GI propeptide. SEQ ID NO:30 is a DNA sequence coding for the SIB propeptide. SEQ ID NO:31 is the amino acid sequence of the SIB propeptide. SEQ ID NO:32 is a DNA sequence coding for the R1 propeptide. SEQ ID NO:33 is the amino acid sequence of the R1 propeptide. SEQ ID NO:34 is a DNA sequence coding for the R1.3 propeptide. SEQ ID NO:35 is the amino acid sequence of the R1.3 propeptide. SEQ ID NO:36 is a DNA sequence coding for the R1.4 propeptide. SEQ ID NO:37 is the amino acid sequence of the R1.4 propeptide. SEQ ID NO:38 is a DNA sequence coding for the Sm1.1 propeptide. SEQ ID NO:39 is the amino acid sequence of the Sm1.1 propeptide. SEQ ID NO:40 is a DNA sequence coding for the SIIA propeptide. SEQ ID NO:41 is the amino acid sequence of the SIIA propeptide. SEQ ID NO:42 is a DNA sequence coding for the S11 peptide. SEQ ID NO:43 is the amino acid sequence of the S11 peptide. SEQ ID NO:44 is a DNA sequence coding for the S2 peptide. SEQ ID NO:45 is the amino acid sequence of the S2 peptide. SEQ ID NO:46 is a DNA sequence coding for the GIB propeptide. SEQ ID NO:47 is the amino acid sequence of the GIB propeptide. SEQ ID NO:48 is a DNA sequence coding for the MnII propeptide. SEQ ID NO:49 is the amino acid sequence of the MnII propeptide. SEQ ID NO:50 is a DNA sequence coding for the A1.2 propeptide. SEQ ID NO:51 is the amino acid sequence of the A1.2 propeptide. SEQ ID NO:52 is a DNA sequence coding for the A1.1 propeptide. SEQ ID NO:53 is the amino acid sequence of the A1.1 propeptide. SEQ ID NO:54 is a DNA sequence coding for the Bt1.6 propeptide. SEQ ID NO:55 is the amino acid sequence of the Bt1.6 propeptide. SEQ ID NO:56 is a DNA sequence coding for the Cn1.1 propeptide. SEQ ID NO:57 is the amino acid sequence of the Cn1.1 propeptide. SEQ ID NO:58 is a DNA sequence coding for the MnI propeptide. SEQ ID NO:59 is the amino acid sequence of the MnI propeptide. SEQ ID NO:60 is a DNA sequence coding for the Cr1.1 propeptide. SEQ ID NO:61 is the amino acid sequence of the Cr1.1 propeptide. SEQ ID NO:62 is a DNA sequence coding for the R1.2 propeptide. SEQ ID NO:63 is the amino acid sequence of the R1.2 propeptide. SEQ ID NO:64 is a DNA sequence coding for the A1.3 propeptide. SEQ ID NO:65 is the amino acid sequence of the A1.3 propeptide. SEQ ID NO:66 is a DNA sequence coding for the A1.7 propeptide. SEQ ID NO:67 is the amino acid sequence of the A1.7 propeptide. SEQ ID NO:68 is a DNA sequence coding for the A1.8 propeptide. SEQ ID NO:69 is the amino acid sequence of the A1.8 propeptide. SEQ ID NO:70 is a DNA sequence coding for the Ay1.1 propeptide. SEQ ID NO:71 is the amino acid sequence of the Ay1.1 propeptide. SEQ ID NO:72 is a DNA sequence coding for the Ay1.1a propeptide. SEQ ID NO:73 is the amino acid sequence of the Ay1.1a propeptide. SEQ ID NO:74 is a DNA sequence coding for the M1.1 propeptide. SEQ ID NO:75 is the amino acid sequence of the M1.1 propeptide. SEQ ID NO:76 is a DNA sequence coding for the M1.3 propeptide. SEQ ID NO:77 is the amino acid sequence of the M1.3 propeptide. SEQ ID NO:78 is a DNA sequence coding for the M1.4 propeptide. SEQ ID NO:79 is the amino acid sequence of the M1.4 propeptide. SEQ ID NO:80 is a DNA sequence coding for the M1.5 propeptide. SEQ ID NO:81 is the amino acid sequence of the M1.5 propeptide. SEQ ID NO:82 is a DNA sequence coding for the O1.3 propeptide. SEQ ID NO:83 is the amino acid sequence of the O1.3 propeptide. SEQ ID NO:84 is a DNA sequence coding for the S1.3 propeptide. SEQ ID NO:85 is the amino acid sequence of the S1.3 propeptide. SEQ ID NO:85 is a DNA sequence coding for the EI propeptide. SEQ ID NO:87 is the amino acid sequence of the EI propeptide. SEQ ID NO:88 is a DNA sequence coding for the EIA propeptide. SEQ ID NO:89 is the amino acid sequence of the EIA propeptide. SEQ ID NO:90 is a DNA sequence coding for the P1.2 propeptide. SEQ ID NO:91 is the amino acid sequence of the P1.2 propeptide. SEQ ID NO:92 is a DNA sequence coding for the P1.3 propeptide. SEQ ID NO:93 is the amino acid sequence of the P1.3 propeptide. SEQ ID NO:94 is a DNA sequence coding for the Sl1.4 propeptide. SEQ ID NO:95 is the amino acid sequence of the Sl1.4 propeptide. SEQ ID NO:96 is a DNA sequence coding for the Sl1.4A propeptide. SEQ ID NO:97 is the amino acid sequence of the Sl1.4A propeptide. SEQ ID NO:98 is a DNA sequence coding for the Sl1.8 propeptide. SEQ ID NO:99 is the amino acid sequence of the Sl1.8 propeptide. SEQ ID NO:100 is a DNA sequence coding for the P1.1 propeptide. SEQ ID NO:101 is the amino acid sequence of the P1.1 propeptide.

DETAILED DESCRIPTION OF THE PREFERRED EMBODIMENT

The invention relates to relatively short peptides (termed α-conotoxins herein), about 10–25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants, for treating benign essential blepharospasm and other forms of focal dystonia and for anti-wrinkle use.

In one aspect, the present invention relates to a method for providing relaxation of muscle. The method involves administering to a patient an effective amount of an α-conotoxin peptide having the general formula set forth above. Exemplary methods involve administering to a patient an effective amount of MI, GI, EI, mono-iodo-MI (Tyr$_{12}$ of MI having an iodine) or di-iodo-MI (Tyr$_{12}$ of MI having two iodines).

The present invention, in another aspect, relates to a pharmaceutical composition comprising an effective amount of an α-conotoxin peptide having the general formula set forth above. Such a pharmaceutical composition has the capability of acting as a neuromuscular non-depolarizing agent, and hence has the capability of acting as a muscle relaxant. Exemplary pharmaceutical compositions acting as neuromuscular non-depolarizing muscle relaxants include as an active ingredient MI, GI, EI, mono-iodo-MI or di-iodo-MI.

The α-conotoxin peptides described herein are sufficiently small to be chemically synthesized. General chemical syntheses for preparing the foregoing α-conotoxin peptides are described hereinafter. Various ones of the α-conotoxin peptides can also be obtained by isolation and purification from specific Conus species using the technique described in U.S. Pat. No. 4,447,356 (Olivera et al., 1984), the disclosure of which is incorporated herein by reference.

Although the α-conotoxin peptides of the present invention can be obtained by purification from cone snails, because the amounts of α-conotoxin peptides obtainable from individual snails are very small, the desired substantially pure α-conotoxin peptides are best practically obtained in commercially valuable amounts by chemical synthesis using solid-phase strategy. For example, the yield from a single cone snail may be about 10 micrograms or less of α-conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active α-conotoxin peptides depends of course upon correct determination of the amino acid sequence.

The α-conotoxin peptides can also be produced by recombinant DNA tecIniques well known in the art. Such techniques are described by Sambrook et al. (1989). The peptides produced in this manner are isolated, reduced if necessary, and oxidized to form the correct disulfide bonds.

One method of forming disulfide bonds in the conantokin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or param-ethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBIHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The FMOC protecting group is removed by treatment with a 20% solution of piperidine in dimethylformamide(DMF). Resins are subsequently washed with DMF (twice), followed by methanol and NMP.

The compounds described herein are used as neurmuscular blocking agents in conjunction with surgery or for intubation of the trachea by conventional parenteral administration e.g., intramuscular or intravenous administration in solution. Thus, the present invention relates to a method for treating a patient during surgical procedures requiring anesthesia and musculoskeletal relaxation. In particular, the method comprises administering to the patient an amount of a compound effective for providing relaxation of muscle. The method involves administering an effective amount of a compound selected from the general formulae which are set forth hereinbefore. The present invention relates to a pharmaceutical composition incorporating a compound described herein or its pharmaceutically acceptable salts.

The manner in which the compounds are administered can vary. Although it is possible to administer the compound in the form of a bulk active chemical, it is preferred to present the compound in the form of a pharmaceutical composition or formulation for parenteral administration. Pharmaceutical compositions containing a compound of the present invention as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an amount of active ingredient effective to provide muscle relaxation will be admixed with a pharmaceutically acceptable carrier.

The pharmaceutical composition also can include various other components as additives or adjuncts. Exemplary pharmaceutically acceptable components or adjuncts include anesthetics, preservatives, antioxidants, bacteriostatic agents, buffering agents, analgesics, anti-inflammatory agents, anti-pyretics, stabilizing agents, thickening agents and suspending agents. Such components can provide additional therapeutic benefit, or act towards preventing any potential side effects which may be posed as a result of administration of the pharmaceutical composition.

Typically, the pharmaceutical composition is administered as an aqueous or non-aqueous solution, as a suspension, or as an emulsion in a pharmaceutically acceptable liquid or mixture of liquids. The compound within the pharmaceutical composition is administered internally by injection or intravenously. For example, the pharmaceutical composition can be administered intravenously as an infusion (e.g., within aqueous dextrose or saline solutions).

Exemplary methods for administering such muscle relaxant compounds (e.g., so as to achieve sterile or aseptic conditions) will be apparent to the skilled artisan. Certain methods suitable for administering compounds useful according to the present invention are set forth in Goodman and Gilman's *The Pharmacological Basis of Therapeutics*, 7th Ed. (1985). The administration to the patient can be intermittent; or at a gradual, continuous, constant or controlled rate. Administration can be to a warm-blooded animal (e.g. a mammal, such as a mouse, rat, cat, rabbit, dog, pig, cow or monkey); but advantageously is administered to a human being. Administration occurs after general anesthesia is administered. The frequency of administration normally is determined by an anesthesiologist, and typically varies from patient to patient.

The dose of the compound is that amount effective to provide a desired effect for a desired time frame. By "effective amount" or "effective dose" is meant that amount parenterally administered (e.g., injected intravenously) sufficient to bind to relevant receptor sites on the musculoskeletal fiber of the patient, and to elicit neuropharmacological effects (e.g., elicit brief depolarization, thus resulting in effective short duration relaxation of skeletal muscle). Short duration typically ranges from about 5 to about 60 minutes.

An effective amount of the compound administered to a patient provides rapid onset and short-lived muscle relaxation. For adult human patients undergoing short surgical procedures, the effective dose of typical compounds injected intravenously generally is from about 0.001 mg/kg to about 0.8 mg/kg body weight, preferably from about 0.05 mg/kg to about 0.5 mg/kg, and more preferably from about 0.05 mg/kg to about 0.3 mg/kg. Following administration of typical compounds in such a concentration range, the onset of paralysis normally develops within 1 to 2 minutes, and is reversible (i.e., muscle tone returns within a short period of time). The compounds of this invention would normally be readministered every 15 to 30 minutes after initial administration or given as a slow continuous infusion depending upon the length of time a muscular block is desired, and as determined by the anesthetist and surgeon in charge of the patient. For adult human patients undergoing long surgical procedures, the effective dose of typical compounds is administered through continuous or intermittent intravenous perfusion at a rate from about 0.001 mg/min to about 0.8 mg/min, preferably from about 0.01 mg/min to about 0.5 mg/min, and more preferably from about 0.01 to about 0.25 mg/min. Following administration of typical compounds in the specified amounts, the onset of paralysis typically develops within 1 to 2 minutes and persists for the duration of the superfusion.

For human patients in the pediatric population undergoing short surgical procedures, the effective dose of typical compounds injected intravenously generally is from about 0.001 mg/kg to about 0.5 mg/kg body weight, preferably from about 0.01 mg/kg to about 0.4 mg/kg, and more preferably from about 0.01 mg/kg to about 0.25 mg/kg. Following administration of typical compounds in such a concentration range, the onset of paralysis normally develops within 1 to 2 minutes, and persists for a short period of time before recovery is achieved. For infants and children undergoing long surgical procedures, the effective dose of typical compounds is administered through continuous or intermittent intravenous perfusion at a rate from about 0.001 mg/min to aobut 0.5 mg/min, preferably from about 0.005 mg/min to about 0.3 mg/ min, and more preferably from about 0.005 mg/min to about 0.2 mg/min. The total amount of drug administered using such a parenteral route of administration generally does not exceed a total of 10 mg, often does not exceed 5 mg and frequently does not exceed 2 mg. Following administration of typical compounds in the specified amounts, the onset of paralysis typically develops within 1 to 2 minutes and persists for the duration of the superfusion.

Such formulations are normally presented in unit dosage forms such as ampoules or disposable injection devices, or in multidose forms such as a bottle from which the appropriate dose may be withdrawn. All such formulations should be rendered sterile.

The compounds of this invention may be presented as a powder e.g., as a unit dose in a sealed vial to which sterile water may be added by a needle, e.g., through a seal thereof (such as rubber). A suitable unit dose to obtain a neuromuscular block for mammals is about 1 mg to 100 mg and most preferably 3 to 50 mg. Thus a suitable pharmaceutical parenteral preparation will preferably contain 20 to 100 mg of the compounds described herein in solution. A pharmaceutical formulation may conventional contain 5 to 400 mg, or 10 to 400 mg, and most preferably 5 to 200 mg of the compounds of this invention. A simple and preferred formulation is a solution of a compound described herein in water which may be prepared by simply dissolving the compound into previously sterilized pure, i. e., pyrogen free water under aseptic conditions and sterilizing the solution. The compounds described herein may also be administered as an infusion of a dextrose solution or a saline solution e.g., Ringers' Solution.

EXAMPLES

The present invention is described by reference to the following Examples, which are offered by way of illustration and are not intended to limit the invention in any manner. Standard techniques well known in the art or the techniques specifically described below were utilized.

Example 1

Dose-Effect Study for MI and GI

This study was an open label, dose-ranging, single center investigation. A total of 14 rats were studied (10 in each of five groups). All animals were anesthetized with pentobarbital (60 mg/kg) given by intraperitoneal administration and maintained with supplemental doses as determined by physiological monitoring variables. A tracheotomy was performed and the rats were ventilated with room air keeping $P_{CO_2}$ near 35 torr. The carotid artery was cannulated to measure blood pressure and arterial blood gases. The right jugular vein was cannulated for intravenous infusion and further drug administration. Body temperature was maintained at 36°–38° C. during the entire experiment. The sciatic nerve was exposed in the popliteal space and stimulated with train-of-four stimulation using a Digistim nerve stimulator. The tivialis anterior muscle contractoin was measured by attaching the rat hind limb to an isometric force transducer to record the evoked response. Prior to administration of the study drug, baseline measurements of blood pressure, heart rate and muscle contraction force were measured for a five-minute period and at five minute intervals for the duration of the study.

The initial dose for analysis was based on biologically effective doses determined in mice. Based on the onset, maximum effect and duration of effect from the first animal studied, the dose for the next animal was either doubled or halved. If the relaxation level was maintained at a maximal level for greater than 20 minutes from this initial dose, then the subsequent dose studied was doubled. This progression continued until the dose that produced near maximal muscle relaxation was found.

The conopeptide derivatives MI and GI were studied in the initial study. For each compound studied, the onset of muacle relaxation, duration of relaxation and an estimate of the $ED_{50}$ was determined from evoked force transducer response. Onset of relaxation is defined as the time for the evoked response to diminish to 5% of pre-drug baseline. In addition, clinical duration, defined as the time from the administration of drug until the evoked muscle response returns to 25% of its pre-drug baseline, and recovery time, defined as tghe time until evoked response returns to 75% of baseline, were also determined. Data were summarized for each compound.

Figure 2:
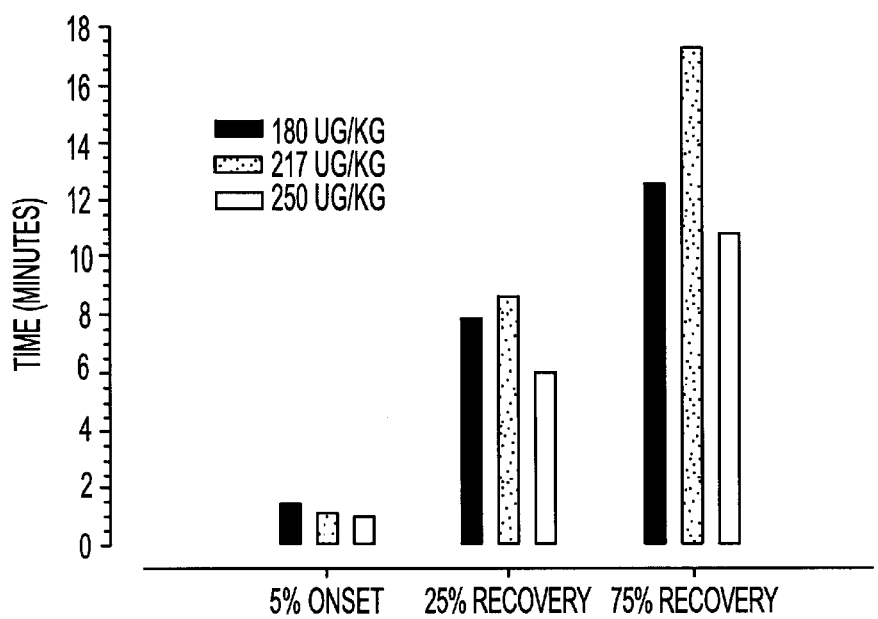
FIG. 2 shows onset and recovery time of neuromuscular block for different doses (180, 217 or 250 μg/kg) of α-conotoxin peptide GI.

The onset and recovery results for both MI and GI are shown in FIGS. 1 and 2, respectively. MI had a shortest onset of 1.46 minutes. The onset time increased with decreasting dose size as is typical for may neuromuscular blocking agents. The recovery time to 25% and 75% of baseline occurred in approximately 8 and 12 minutes, respectively. These recovery times were constant for doses over 100 µg/kg, which implies that recovery of thge drug effects is very rapid and not easily saturated in its capacity. Anesthetic drugs that behave in similar fashion tend to be degraded by chemical or enzymatic processes in the body rather than by metabolic organ transformation.

GI had a shorter onset time of just under 1 minute. The time for 25% and 75% recovery of baseline was in the range of 8 and 15 minutes, respectively. As with MI, increasing the dose tended to shorten the onset time without extending the recovery times dramatically. For GI, the onset time was similar to that seen with succinylcholine. The recovery times for both agents were similar to succinylcholine.

A comparison of these results to onset and recovery times for other clinically available neuromuscular blocking agents is shown in Table 1.

TABLE 1

Comparison of Neuromuscular Blocking Agents

| Agent (mg/kg) | Onset Time (sec) | Recovery (min) 25% | 75% |
|---|---|---|---|
| MI (0.15) | 90 | 8 | 12 |
| GI (0.2) | 60–70 | 6–8 | 10–15 |

TABLE 1-continued

Comparison of Neuromuscular Blocking Agents

| Agent (mg/kg) | Onset Time (sec) | Recovery (min) 25% | 75% |
|---|---|---|---|
| Sux (1.0) | 60 | 5–7 | 10 |
| Org 9847 (1.5) | 80 | 8 | 15 |
| Rocuronium (0.6) | 80 | 40 | 60 |
| Mivacurium (0.2) | 150 | 20 | 27 |
| Vecuronium (0.1) | 120–180 | 40 | 60 |
| Cisatracurium (0.1) | 120–180 | 45 | 60–70 |

Figure 3:
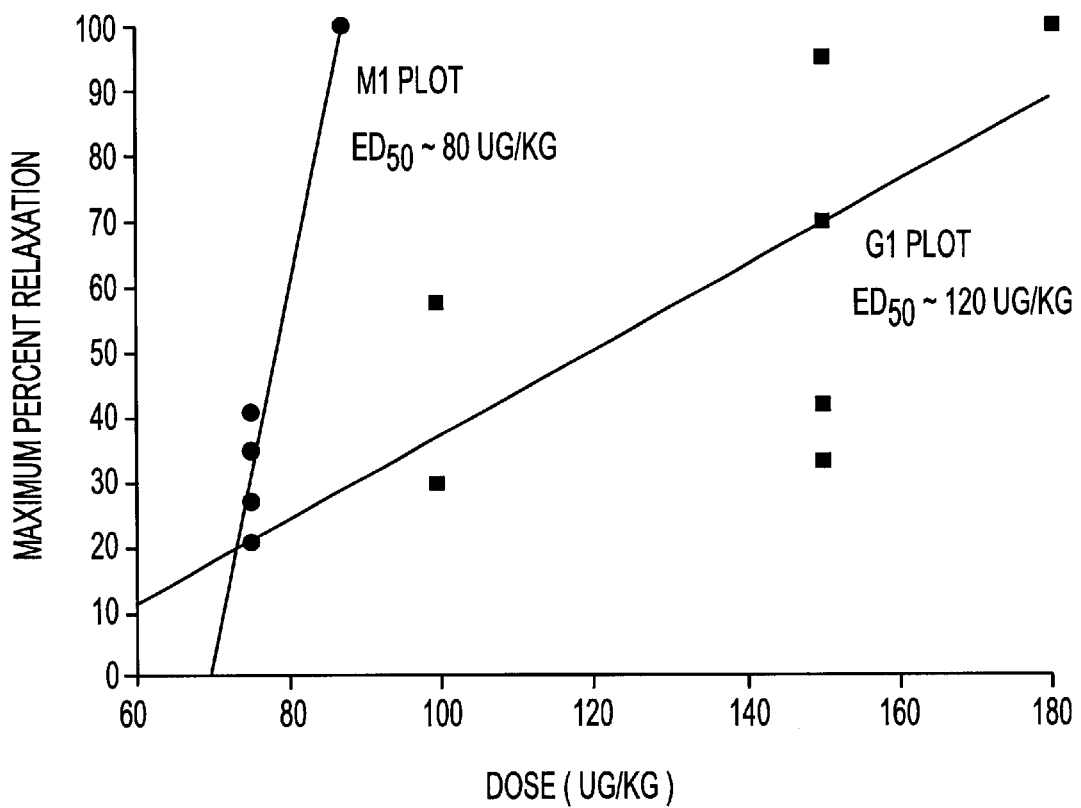
FIG. 3 shows dose response curves for the α-conotoxin peptides MI (●) and GI (■).

For doses of these agents which produced less than maximum levels of neuromuscular block, dose-response plots can be determined to estimate the $ED_{50}$ dose of these agents. In this context, $ED_{50}$ refers to the dose of agent which is expected to produce half of the maximum relaxation level. The data of this initial study (FIG. 3) shows that GI is less potent than MI as reflected in the lower $ED_{50}$ value for MI (~80 µg/kg for MI compared to ~120 µg/kg for GI).

These results show that α-conotoxin peptides are biologically active at the neuromuscular junction producing skeletal muscle paralysis that mimics the repsonse seen with non-depolarizing neuromuscular blocking agents given during anesthesia. The onset and duration of relaxation is rapid and short which is highly desirable for a number of clinical reasons. In this regard, with the rapid onset time, short duration and no prolongation of drug effect with large doses, the clinical benefit of the α-conotoxin peptides exceeds the currently available non-depolarizing neuromuscular blocking agents. In addition to their desirable effect profile, the α-conotoxin peptides appear to have no significant cardiovascular effects on administration. Thus, the desirable effect profile with minimal side effects are desirable clinical properties for the α-conotoxin peptides.

Example 2

Dose-Effect Study for Iodinated-MI

Figure 4:
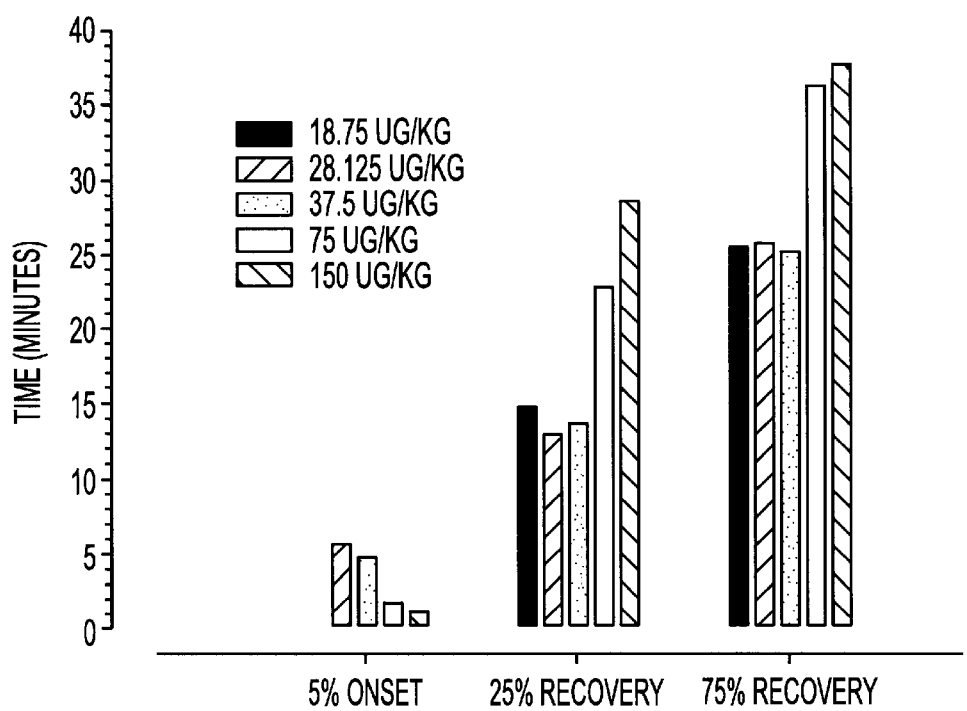
FIG. 4 shows onset and recovery time of neuromuscular block for different doses (18.76, 28.125, 37.5, 75 or 150 μg/kg) of the α-conotoxin peptide mono-iodo-$Tyr_{12}$-MI.
Figure 5:
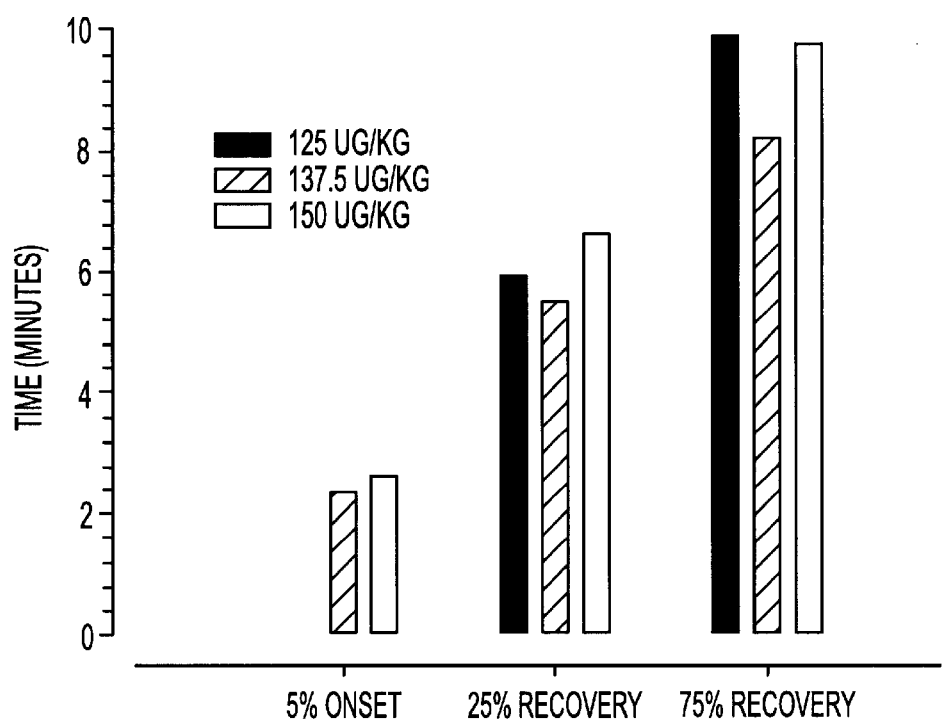
FIG. 5 shows onset and recovery time of neuromuscular block for different doses (125, 137.5 or 150 μg/kg) of the α-conotoxin peptide di-iodo-$Tyr_{12}$-MI.
Figure 6:
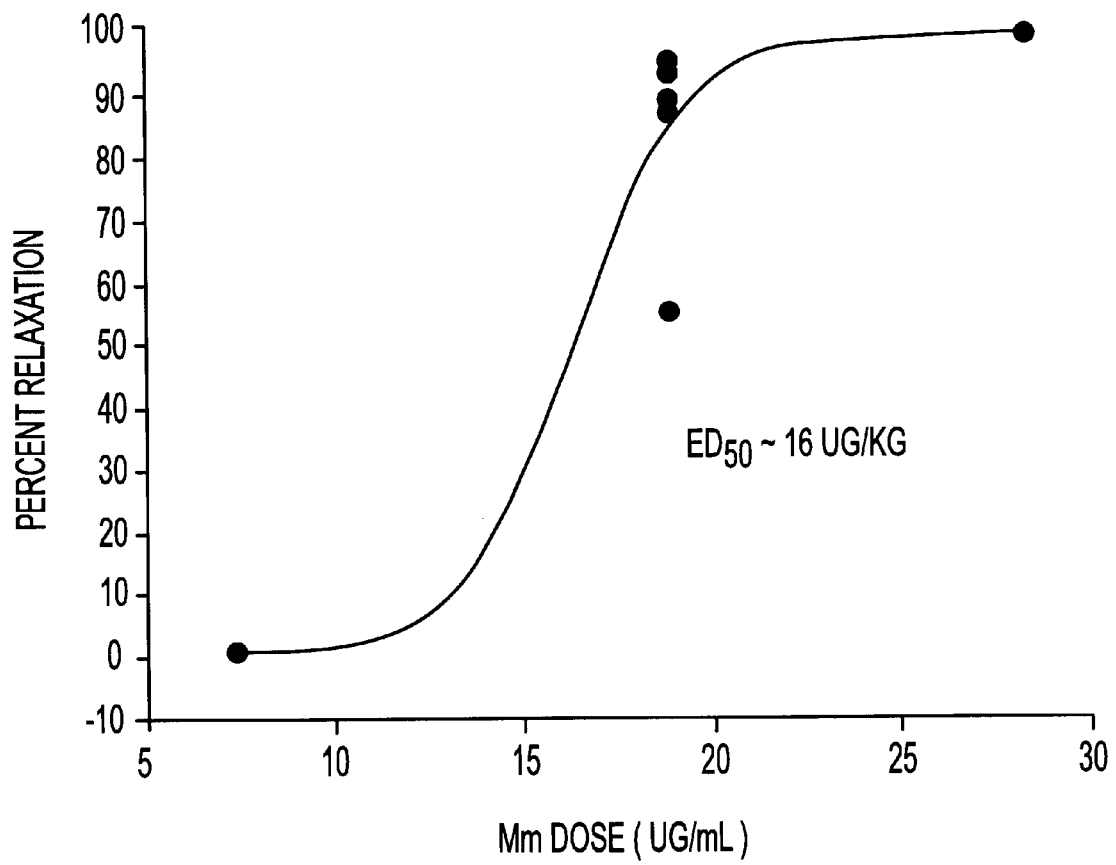
FIG. 6 shows dose response curve for the α-conotoxin peptide mono-iodo-$Tyr_{12}$-MI.
Figure 7:
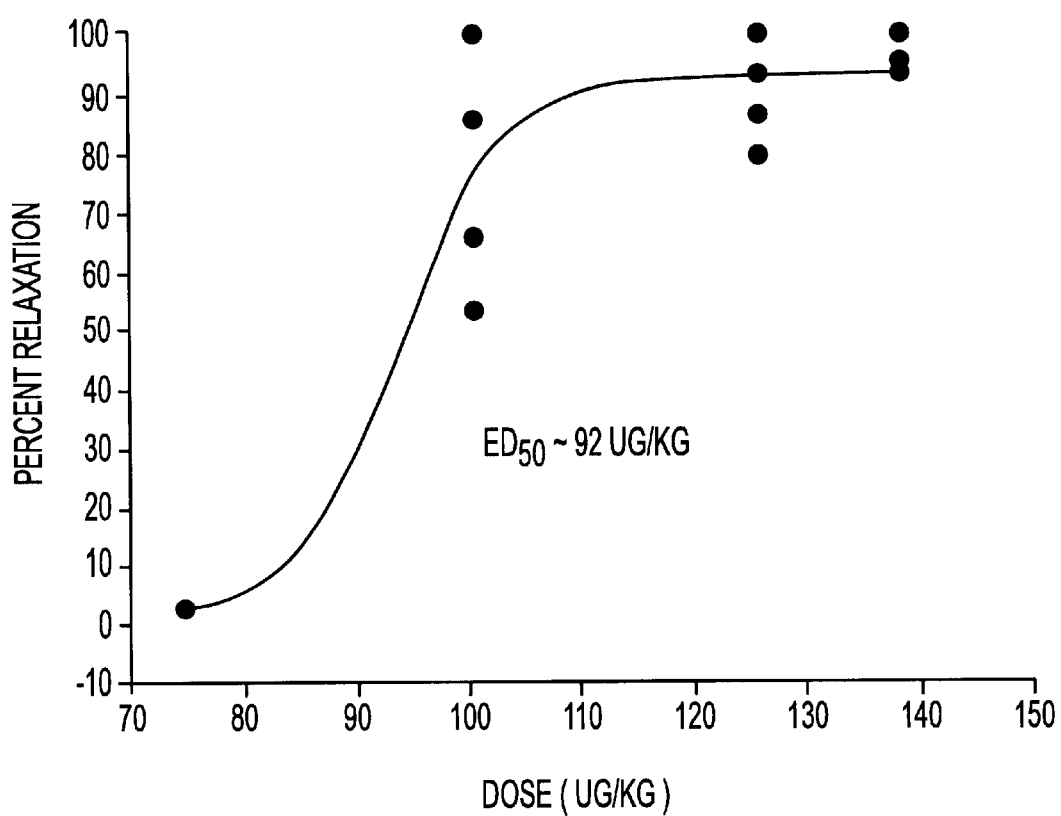
FIG. 7 shows dose response curve for the α-conotoxin peptide di-iodo-Tyr$_{12}$-MI.

A similar study as described in Example 1 was conducted for two iodinated derivatives of MI, namely, mono-iodo-$Tyr_{12}$-MI and di-iodo-$Tyr_{12}$-MI. The onset and recovery results for mono-iodo-$Tyr_{12}$-MI and di-iodo-$Tyr_{12}$-MI are shown in FIGS. 4 and 5, respectively. Dose-response plots for mono-iodo-$Tyr_{12}$-MI and di-iodo-$Tyr_{12}$-MI were made to estimate the $ED_{50}$ dose of these agents. The $ED_{50}$ values are ~16 µg/kg for mono-iodo-$Tyr_{12}$-MI and 92.5 µg/kg for di-iodo-$Tyr_{12}$-MI.

Example 3

Muscle Relaxant Effect in Anesthetized Monkeys

The peptides MI, GI, EI, mono-iodo-MI and di-iodo-MI are each separately dissolved 0.9 percent saline at a concentration of 2 mg/ml. Rhesus monkeys are anesthetized with halothane, nitrous oxide and oxygen. The maintenance concentration of halothane is 1.0%. Arterial and venous catheters are placed in the femoral vessels for drug administration and recording of the arterial pressure. Controlled ventilation is accomplished via an endotrachael tube. Twitch and tetanic contractions of the tibialis anterior muscle are elicited indirectly via the sciatic nerve. Recordings of arterial pressure electrocardiogram (lead I), heart rate, and muscle function are made simultaneously. Four to six animals received each listed compound. Four additional animals received succinylcholine chloride or d-tubocurarine chloride as controls. Is is seen that the tested compounds generally provide similar or better results than those seen for succinylcholine chloride or d-tubocurarine chloride.

Example 4

Isolation of DNA Encoding α-Conotoxins

DNA coding for α-conotoxins was isolated and cloned in accordance with conventional techniques using general procedures well known in the art, such as described in Olivera et al. (1996). Alternatively, cDNA libraries was prepared from Conus venom duct using conventional techniques. DNA from single clones was amplified by conventional techniques using primers which correspond approximately to the M13 universal priming site and the M13 reverse universal priming site. Clones having a size of approximately 300 nucleotides were sequenced and screened for similarity in sequence to known α-conotoxins. The DNA sequences and encoded propeptide or peptide sequences are set forth in Tables 2–26. It was discovered that the following mature α-conotoxin peptides had the same sequence: (a) R1.4, A1.1, Bt1.6, Cn1.1 and MnI; and (b) Sm1.1 and Cr1.1.

TABLE 2

DNA Sequence (SEQ ID NO:28) and Protein Sequence
(SEQ ID NO:29) of GI

| atg | ttc | acc | gtg | ttt | ctg | ttg | gtg | gtc | ttg | gca | acc | act | gtc | gtt | tcc |
|-----|-----|-----|-----|-----|-----|-----|-----|-----|-----|-----|-----|-----|-----|-----|-----|
| Met | Phe | Thr | Val | Phe | Leu | Leu | Val | Val | Leu | Ala | Thr | Thr | Val | Val | Ser |

| ttc | cct | tca | gaa | cgt | gca | tct | gat | ggc | agg | gat | gac | aca | gcc | aaa | gac |
|-----|-----|-----|-----|-----|-----|-----|-----|-----|-----|-----|-----|-----|-----|-----|-----|
| Phe | Pro | Ser | Glu | Arg | Ala | Ser | Asp | Gly | Arg | Asp | Asp | Thr | Ala | Lys | Asp |

| gaa | ggg | tct | gac | atg | gag | aaa | ttg | gtc | gag | aaa | aaa | gaa | tgt | tgc | aat |
|-----|-----|-----|-----|-----|-----|-----|-----|-----|-----|-----|-----|-----|-----|-----|-----|
| Glu | Gly | Ser | Asp | Met | Glu | Lys | Leu | Val | Glu | Lys | Lys | Glu | Cys | Cys | Asn |

| cct | gcc | tgt | ggc | aga | cac | tac | agt | tgt | gga | cgc | tgatgctcca | ggaccctctg |
|-----|-----|-----|-----|-----|-----|-----|-----|-----|-----|-----|------------|------------|
| Pro | Ala | Cys | Gly | Arg | His | Tyr | Ser | Cys | Gly | Arg | | | aaccacggac gtgccgccct ctgcctgacc tgcttcactg tccgtctctt tgtgccacta
gaactgaaca gctcgatcca ctagactacc acgttacctc cgtgttctaa aactacttgg
tttagattgc ctttaatttc tagtcatact tcctgttatt acgtcgtcca aaattgaaac
aagaacatga ggggtgtcag ctcaaacaaa atcaggcaat gacaaggaaa atgtctccga
tcgatccgaa aactgtcacc cgtcactctc ttaaccagtt ttagaactga ttaccactag
agcttttgta ccacatcaaa tcaggtctat gtgtgatgtt tcttttgcaa aatttaattt
ttgagaaaaa aagctcaaaa tgtgggaagt gcttttgatt ttctgacaac ttgtgatcat
gtccgttttc agtgagtcta attgcaacct ctgtgtgatt ttcttcacct gttaagcaac
gcaaagaggt tgtccataac caggaaagca acagacaaag aaatgcttga gaatttcagg
ttatagataa ggtaaggaaa aaaggagag ctatgggaaa tgatgaaaac aacagataaa
ataaattgaa cagtacctac ttgtttcatg gttgattttt ttttctctga ataatctctg
tggacactaa tggcagtctc tcctcacccc acgccattag taagcttatt ttttctttct
ttatccaaga tttgctgaac atatttagcc ta9atataga cattgctaca tatataatct
gacaataaac tttcatgggc accaatt

TABLE 3

DNA Sequence (SBQ ID NO:30) and Protein Sequence
(SEQ ID NO:31) of SIB

| atg | ttc | acc | gtg | ttt | ctg | ttg | gtt | grc | ttg | gca | acd | act | gtc | grt | tcc |
|-----|-----|-----|-----|-----|-----|-----|-----|-----|-----|-----|-----|-----|-----|-----|-----|
| Met | Phe | Thr | Val | Phe | Leu | Leu | Val | Val | Leu | Ala | Thr | Thr | Val | Val | Ser |

| ttc | cct | tca | gat | cgt | gca | tct | gat | ggc | agg | gat | gac | gaa | gcc | aaa | gac |
|-----|-----|-----|-----|-----|-----|-----|-----|-----|-----|-----|-----|-----|-----|-----|-----|
| Phe | Pro | Ser | Asp | Arg | Ala | Ser | Asp | Gly | Arg | Asp | Asp | Glu | Ala | Lys | Asp |

| gaa | agg | tct | gac | atg | cac | gaa | tcg | gac | cgg | aaa | gaa | atc | tgt | tgc | aat |
|-----|-----|-----|-----|-----|-----|-----|-----|-----|-----|-----|-----|-----|-----|-----|-----|
| Glu | Arg | Ser | Asp | Met | His | Glu | Ser | Asp | Arg | Lys | Glu | Ile | Cys | Cys | Asn |

| cct | gcc | tgt | ggc | cca | aag | tat | agt | tgt | gga | cgc | tgatgctcca | ggaccctctg |
|-----|-----|-----|-----|-----|-----|-----|-----|-----|-----|-----|------------|------------|
| Pro | Ala | Cys | Gly | Pro | Lys | Tyr | Ser | Cys | Gly | Arg | | | aacc

TABLE 4

DNA Sequence (SEQ ID NO:32) and Protein Sequence
(SEQ ID NO:31) of R1

| atg | ttc | acc | gtg | ttt | ctg | ttg | gtt | gtc | ttg | aca | atc | act | gtc | gtt | tcc |
|-----|-----|-----|-----|-----|-----|-----|-----|-----|-----|-----|-----|-----|-----|-----|-----|
| Met | Phe | Thr | Val | Phe | Leu | Leu | Val | Val | Leu | Thr | Ile | Thr | Val | Val | Ser |

TABLE 4-continued

DNA Sequence (SEQ ID NO:32) and Protein Sequence (SEQ ID NO:31) of R1

```
ttc cct tca gat cgt gca tct gat ggc agg gat gac gaa gcc aaa gac
Phe Pro Ser Asp Arg Ala Ser Asp Gly Arg Asp Asp Clu Ala Lys Asp gaa agg tct gac atg tac aaa tcg aaa cgg aat gga cgc tgt tgc car
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Cly Arg aaccacgacg t
```

TABLE 5

DNA Sequence (SEQ ID NO:34) and Protein Sequence (SEQ ID NO:35) of R1.3

```
atg ttc acc gtg ttt ctg ttg gtg gtc ttg gca acc act gtc gtt tcc
Met Phe Thr Val Phe Leu Leu Val Val Leu Ala Thr Thr Val Val Ser ttc cct tca gaa cgt gca tct gat ggc agg gat gac aca gcc aaa gac
Phe Pro Ser Glu Arg Ala Ser Asp Gly Arg Asp Asp Thr Ala Lys Asp gaa ggg tct gac atg gag aaa ttg gtc gag aaa aaa gaa tgt tgc aat
Glu Cly Ser Asp Met Glu Lys Leu Val Glu Lys Lys Glu Cys Cys Asn cct gcc tgt ggc aga cac tac agt tgt aag gga ggacgctgat gctccagacc
Pro Ala Cys Gly Arg His Tyr Ser Cys Lys Gly ctctgaacca cgacgt
```

TABLE 6

DNA Sequence (SEQ ID NO:36) and Protein Sequence (SEQ ID NO:37) of R1.4

```
atg ttc acc gtg ttt ctg ttg gtt gtc ttg aca atc act gtc gtt tcc
Met Phe Thr Val Phe Leu Leu Val Val Leu Thr Ile Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Cly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t
```

TABLE 7

DNA Sequence (SBQ ID NO:28) and Protein Sequence (SEQ ID NO:39) of Sm1.1

```
atg ttc acc gtg ttt ctg ttg gtt gtc ttg gca acc act gtc gtt tcc
Met Phe Thr Val Phe Leu Leu Val Val Leu Ala Thr Thr Val Val Ser ttc cct tca gat cgt gca tct gat ggc agg gat gac gcc aaa gac
Phe Pro Ser Asp Arg Ala Ser Asp Gly Arg Asp Asp Glu Ala Lys Asp gaa agg tct gac atg cac gaa tcg ggc cgg aaa gga cgc gga cgc tgt
Glu Arg Ser Asp Met His Glu Ser Gly Arg Lys Gly Arg Gly Arg Cys tgc cat cct gcc tgt ggc cca aac tat agt tgt ggacgctgat gctccaggac
Cys His Pro Ala Cys Gly Pro Asn Tyr Ser Cys
```

TABLE 7-continued

DNA Sequence (SBQ ID NO:28) and Protein Sequence (SEQ ID NO:39) of Sm1.1 cqtctgaacc acgacgt tgc cat cct gcc tgt ggc cca aac tat agt tgt ggacgctgat gctccaggac
Cys His Pro Ala Cys Gly Pro Asn Tyr Ser Cys cqtctgaacc acgacgt

TABLE 8

DNA Sequence (SEQ ID NO:40) and Protein Sequence (SEQ ID NO:41) of SIIA atg ttc acc gtg ttt ctg ttg gtt gtc ttg gca act act gtc gtt tcc
Met Phe Thr Val Phe Leu Leu Val Val Leu Ala Thr Thr Val Val Ser ttc cct tca gat cgt gca tct gat ggc agg gat gac gaa gcc aaa gac
Phe Prc Ser Asp Arg Ala Ser Asp Cly Arg Asp Asp Clu Ala Lys Asp gaa agg tct gac atg cac gaa tcg gac cgg aat gga cgc gga tgc cgt
Glu Arg Ser Asp Met His Glu Ser Aap Arg Asn Gly Arg Gly Cys Cys tgc aat cct gcc tgt ggc cca aac tat ggt tgt ggc acc tca tgc tcc
Cys Asn Pro Ala Cys Gly Pro Asn Tyr Cly Cys Gly Thr Ser Cys Ser agg acc ctc tgaaccacga cgttcgagca
Arg Thr Leu

TABLE 9

DNA Sequence (SEQ ID NO:42) and Protein Sequence (SEQ ID NO:43) of S11 tgt tgc cat cct gcc tgt ggc aga aag tat aat tgt
Cys Cys His Pro Ala Cys Gly Arg Lys Tyr Asn Cys gga cgc tga
Gly Arg

TABLE 10

DNA Sequence (SEQ ID NO:44) and Protein Sequence (SEQ ID NO:45) of S2 tgc tgt tgc aat cct gcc tgt ggc cca aac tat ggt
Cys Cys Cys Asn Pro Ala Cys Gly Pro Asn Tyr Gly tgt ggc acc tca tgc tcc aga ccc tct gaa cca cga
Cys Gly Thr Ser Cys Ser Arg Pro Ser Glu Pro Arg cgt tag
Arg

TABLE 11

DNA Sequence (SEQ ID NO:46) and Protein Sequence (SEQ ID NO:47) of GIB atg ttc acc gtg ttt ctg ttg gtg gtc ttg gca acc act gtc gtt tcc
Met Phe Thr Val Phe Leu Leu Val Val Leu Ala Thr Thr Val Val Ser ttc cct tca gaa cgt gca tct gat ggc agg gat gac aca gcc aaa gac
Phe Pro Ser Glu Arg Ala Ser Aap Gly Arg Asp Asp Thr Ala Lys Asp gaa ggg tct gac atg gag aaa ttg gtc gag aaa aaa gaa rgt tgc aat
Glu Gly Ser Asp Met Glu Lys Leu Val Glu Lys Lys Glu Cys Cys Asn cct gcc tgt ggc aga cac tac agt tgt aag gga ggacgctgat gctccaggac
Prc Ala Cys Gly Arg His Tyr Ser Cys Lys Gly cctctgaacc acggacgtgc cgccctctgc ctgacctgct tcactgtccg tctctttgtg
ccactagaac tgaacagctc gatccactag actaccacgt tacctccgtg ttctaaaact
acttggttta gattgccttt aatttctagt catacttcct gttattacgt cgtccaaaat
tgaaacaaga acatgagggg tgtcagctca aacaaaatca ggcaatgaca aggaaaatgt

TABLE 11-continued

DNA Sequence (SEQ ID NO:46) and Protein Sequence (SEQ ID NO:47) of GIB

```
ctccgatcga tccgaaaact gtcacccgtc actctcttaa ccagttttag aactgattac
cactagagct tttgtaccac atcaaatcag gtctatgtgt gatgtttctt ttgcaaaatt
taattttga gaaaaaagc tcaaaatgtg ggaagtgctt ttgattttct gacaacttgt
gatcatgtcc gttttcagtg agtctaattg caacctctgt gtgattttct tcacctgtta
agcaacgcaa agaggttgtc cataaccagg aaagcaacag acaaagaaat gcttgagaat
ttcaggttat agataaggta aggaaaaaaa ggagagctat gggaaatgat gaaaacaaca
gataaaataa attgaacagt acctactgt ttcatggttg attttttttt ctctgaataa
tctctgtgga cactaatggc agtctctcct caccccacgc cattagtaag cttatttttt
ctttctttat ccaagatttg ctgaacatat ttagcctaga tatagacatt gctacatata
taatctgaca ataaactttc atgggcacca att
```

TABLE 12

DNA Sequence (SEQ ID NO:48) and Protein Sequence (SEQ ID NO:49) of MnII

```
atg ttc acc gtg ttt ctg ttg gtt gtc ttg aca acc act gtc gtt tcc
Met Phe Thr Val Phe Leu Leu Val Val Leu Thr Thr Thr Val Val Ser ttc cct tca gat agt gca tct ggt ggc agg gat gac gag gcc aaa gac
Phe Pro Ser Asp Ser Ala Ser Gly Gly Arg Asp Asp Glu Ala Lys Asp gaa agg tct gac arg tac gaa ttg aaa cgg aat gga cac tgt tgc cat
Glu Arg Ser Asp Met Tyr Glu Leu Lys Arg Asn Gly His Cys Cys His cct gcc tgt ggt ggc aaa tac gtt aaa tgt gga cgc tgatgctcca
Pro Ala Cys Gly Gly Lys Tyr Val Lys Cys Gly Arg ggaccctctc gaaccacg
```

TABLE 13

DNA Sequence (SEQ ID NO:50) and Protein Sequence (SEQ ID NO:50) of A1.2

```
atg ttc acc gtg ttt ctg ttg gtt gtc ttg aca acc act gtc gtt tcc
Met Phe Thr Val Phe Leu Leu Val Val Leu Thr Thr Thr Val Val Ser ttc cct tca gat agt gca tct ggt ggc agg gat gac gag gcc aaa gac
Phe Pro Ser Asp Ser Ala Ser Gly Gly Arg Asp Asp Glu Ala Lys Asp gaa agg tct gac arg tac gaa ttg aaa cgg aat gga cac tgt tgc cat
Glu Arg Ser Asp Met Tyr Glu Leu Lys Arg Asn Gly His Cys Cys His cct gcc tgt ggt ggc aaa tac gtt aaa tgt gga cgc tgatgctcca
Pro Ala Cys Gly Gly Lys Tyr Val Lys Cys Gly Arg ggaccctctc gaaccacg
```

TABLE 14

DNA Sequence (SEQ ID NO:52) and Protein Sequence (SEQ ID NO:53) of A1.1

```
atg ttc acc gtg ttt ctg ttg gtt gtc ttg aca aca act gtc gtt tcc
Met Phe Thr Val Phe Leu Leu Val Val Leu Thr Thr Thr Val Val Ser tac cct tca gat agt gca tct gat ggc agg gat gac gaa gcc aaa gac
Tyr Pro Ser Asp Ser Ala Ser Asp Gly Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Gly Arg Cys Cys His
```

TABLE 14-continued

DNA Sequence (SEQ ID NO:52) and Protein Sequence (SEQ ID NO:53) of A1.1 cct gcc tgt ggc aaa cac ttt agt tgt gga cgc tgatgctcca ggaccctctg
Pro Ala Cys Gly Lys His Phe Ser Cys Gly Arg aaccacgacg t

TABLE 15

DNA Sequence (SEQ ID NO:54) and Protein Sequence (SEQ ID NO:55) of Bt1.6 atg ttc acc gtg ttt ctg ttg gtt gtc ttg gca acc act gtc gtt tcc
Met Phe Thr Val Phe Leu Leu Val Val Leu Ala Thr Thr Val Val Ser tac cct tca gat agt gca tct gat ggc agg gat gac gaa acc aaa gac
Tyr Pro Ser Asp Ser Ala Ser Asp Gly Arg Asp Asp Glu Thr Lys Asp gaa aag tct gac atg tac aaa tcg aaa cgg aat gga cgc tgt tgc cat
Glu Lys Ser Asp Met Tyr Lys Ser Lys Arg Asn Gly Arg Cys Cys His cct gcc tgt ggc aaa cac ttt agt tgt gga cgc tgatgctgca ggaccctctg
Pro Ala Cys Gly Lys His Phe Ser Cys Gly Arg aaccacgacg t

TABLE 16

DNA Sequence (SEQ ID NO:56) and Protein Sequence (SEQ ID NO:57) of Cn1.1 atg ttc acc gtg ttt ctg ttg gtt gtc ttg aca acc act gtc gtt tcc
Met Phe Thr Val Phe Leu Leu Val Val Leu Thr Thr Thr Val Val Ser ttc cct tca gat agt gca tct gat gtc agg gat gac gaa gcc aaa gac
Phe Pro Ser Asp Ser Ala Ser Asp Val Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t

TABLE 17

DNA Sequence (SEQ ID NO:58) and Protein Sequence (SEQ ID NO:59) of MnI atg ttc acc gtg ttt ctg ttg gtt gtc ttg aca aca act gtc gtt tcc
Met Phe Thr Val Phe Leu Leu Val Val Leu Thr Thr Thr Val Val Ser tac cct tca gat agt gca tct gat ggc agg gat gac gaa gcc aaa gac
Tyr Pro Ser Asp Ser Ala Ser Asp Gly Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t

TABLE 18

DNA Sequence (SEQ ID NO:60) and Protein Sequence (SEQ ID NO:61) of Cr1.1

| | | | | | | | | | | | | | |
|---|---|---|---|---|---|---|---|---|---|---|---|---|---|
| atg | ttc | acc | gtg | ttt | ctg | ttg | gtt | gtc | ttg | gca | gcc | act | gtc gtt tcc |
| Met | Phe | Thr | Val | Phe | Leu | Leu | Val | Val | Leu | Ala | Ala | Thr | Val Val Ser |
| ttc | cct | tca | gat | cgt | gca | tct | gat | ggc | agg | gat | gac | gaa | gcc aaa gac |
| Phe | Pro | Ser | Asp | Arg | Ala | Ser | Asp | Gly | Arg | Asp | Asp | Glu | Ala Lys Asp |
| gaa | aga | tct | gac | atg | cac | gaa | tcg | gac | cgg | aaa | gga | cgc | gga cgc tgt |
| Glu | Arg | Ser | Asp | Met | His | Glu | Ser | Asp | Arg | Lys | Gly | Arg | Gly Arg Cys |
| tgc | cat | cct | gcc | tgt | ggc | cca | aat | tat | agt | tgt | gga | cgc | tgatgctcca |
| Cys | His | Pro | Ala | Cys | Gly | Pro | Asn | Tyr | Ser | Cys | Gly | Arg | | ggaccctctg aaccacgacg

TABLE 19

DNA Sequence (SEQ ID NO:62) and Protein Sequence (SEQ ID NO:63) of R1.2

| | | | | | | | | | | | | | |
|---|---|---|---|---|---|---|---|---|---|---|---|---|---|
| atg | ttc | acc | gtg | ttt | ctg | ttg | gtg | gtc | ttg | gca | acc | act | gtc gtt tcc |
| Met | Phe | Thr | Val | Phe | Leu | Leu | Val | Val | Leu | Ala | Thr | Thr | Val Val Ser |
| ttc | cct | tca | gaa | cgt | gca | tct | gat | ggc | agg | gat | gac | aca | gcc aaa gac |
| Phe | Pro | Ser | Glu | Arg | Ala | Ser | Asp | Gly | Arg | Asp | Asp | Thr | Ala Lys Asp |
| gaa | ggg | tct | gac | atg | gac | aaa | ttg | gtc | gag | aaa | aaa | gaa | tgt tgc cat |
| Glu | Gly | Ser | Asp | Met | Asp | Lys | Leu | Val | Glu | Lys | Lys | Glu | Cys Cys His |
| cct | gcc | tgt | ggc | aaa | cac | ttc | agt | tgt | gga | cgc | tgatgctcca | ggaccctctg | |
| Pro | Ala | Cys | Gly | Lys | His | Phe | Ser | Cys | Gly | Arg | | | | aaccacgacg t

TABLE 20

DNA Sequence (SEQ ID NO:64) and Protein Sequence (SEQ ID NO:65) of A1.3 tct gat ggc agg gat gac gaa gcc aaa gac gaa agg
Ser Asp Gly Arg Asp Asp Glu Ala Lys Asp Glu Arg tct gac atg tac aaa tcg aaa cgg aat gga cgc tgt
Ser Asp Met Tyr Lys Ser Lys Arg Asn Gly Arg Cys tgc cac cct gcc tgt ggc aaa cactttatt tgt gga
Cys His Pro Ala Cys Gly Lys His Phe Ile Cys Gly cgc tga
Arg

TABLE 21

DNA Sequenee (SEQ ID NO:66) and Protein Sequence (SEQ ID NQ:67) of A1.7 tct ggt ggc agg gat gac gaa gcc aaa gac gaa agg
Ser Gly Gly Arg Asp Asp Glu Ala Lys Asp Glu Arg tct gac atg tac gaa tcg gac cgg aat gga cgc tgt
Ser Asp Met Tyr Glu Ser Asp Arg Asn Gly Arg Cys

TABLE 21-continued

DNA Sequenee (SEQ ID NO:66) and Protein Sequence (SEQ ID NQ:67) of A1.7 tgc cat cct gcc tgt ggc aaa cacttt agt tgt gga
Cys His Pro Ala Cys Gly Lys His Phe Ser Cys Gly cgc tga
Arg

TABLE 22

DNA Sequence (SEQ ID NO:68) and Protein Sequence (SEQ ID NO:69) of A1.8 tct gat ggc agg gat gac gaa gcc aaa gac aaa agg
Ser Asp Gly Arg Asp Asp Glu Ala Lys Asp Lys Arg tct gac atg tac gaa tcg gac cgg aat gga cgc tgt
Ser Asp Met Tyr Glu Ser Asp Arg Asn Gly Arg Cys tgc cat cct tcc tgt ggc aga aag tat aat tgt gga
Cys His Pro Ser Cys Gly Arg Lys Tyr Asn Cys Gly cgc tga
Arg

TABLE 23

DNA Sequence (SEQ ID NO:70) and Protein Sequence (SEQ ID NO:71) of Ay1.1 tctgatggca gggatgacga agccaaagac gaaaggtctg acatgtac gaa tcg gac
Glu Ser Asp cgg aat gga cgc tgt tgc cat cct gcc tgt gcg aga aag tat aat tgt
Arg Asn Gly Arg Cys Cys His Pro Ala Cys Ala Arg Lys Tyr Asn Cys gga cgc rgatgctcca ggaccctctg aaccacgacg t
Gly Arg

TABLE 24

DNA Sequence (SEQ ID NO:72) and Protein Sequence (SEQ ID NO:73) of Ay1.1a tctgatggca gggatgacga agccaaagac gaaaggtctg acatgtac gaa tcg gag
Glu Ser Glu cgg aat gaa cgc tgt tgc cat cct gcc tgt gcg aga aag tat aat tgt
Arg Asn Glu Arg Cys Cys His Pro Ala Cys Ala Arg Lys Tyr Asn Cys gga cgc tgatgctcca ggaccctctg aaccacgacg t
Gly Arg

TABLE 25

DNA Sequence (SEQ ID NO:74) and Protein Sequence (SEQ ID NO:75) of M1.1 atg ttc acc gtg ttt ctg ttg gtt gtc ttg aca acc act gtc gtt tcc
Met Phe Thr Val Phe Leu Leu Val Val Leu Thr Thr Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg tac gaa tcg aaa cgg gat gga cgc tgt tgc cat
Glu Arg Ser Asp Met Tyr Glu Ser Lys Arg Asp Gly Arg Cys Cys His cct gcc tgt ggg caa aac tat agt tgt gga cgc tgatgctcca ggaccctctg
Pro Ala Cys Gly Gln Asn Tyr Ser Cys Gly Arg aaccacgacg t

TABLE 26

DNA Sequence (SEQ ID NO:76) and Protein Sequence (SEQ ID NO:77) of M1.3 tct gat ggc agg gat gac gaa gcc aaa gac gaa agg cct gac atg tac
Ser Asp Gly Arg Asp Asp Glu Ala Lys Asp Glu Arg Pro Asp Met Tyr aaa tcg aaa cgg gat gga cgc tgt tgc cat cct gcc tgt gcg aaa cac
Lys Ser Lys Arg Asp Gly Arg Cys Cys His Pro Ala Cys Ala Lys His ttt aat tgt gga cgc tgatgctcca ggaccctctg aaccacgacg t
Phe Asn Cys Gly Arg

TABLE 27

DNA Sequence (SEQ ID NO:78) and Protein Sequence (SEQ ID NO:79) of M1.4

```
tct gar ggc agg gat gac gaa gcc aaa gac gaa agg tct gac atg tac
Ser Asp Gly Arg Asp Asp Glu Ala Lys Asp Glu Arg Ser Asp Met Tyr gaa tcg aaa cgg aat gga cgc tgt tgc cat cct gcc tgt gcg aaa aac
Glu Ser Lys Arg Asn Gly Arg Cys Cys His Pro Ala Cys Ala Lys Asn tat agt tgt gga cgc tgatgctcca ggaccctctg aaccacgacg t
    Tyr Ser Cys Gly Arg
```

TABLE 28

DNA Sequenee (SEQ ID NO:80) and Protein Sequence (SEQ ID NO:81) of M1.5

```
tct gat ggc agg gat gac gaa gcc aaa gac gaa agg tct gac atg tac
Ser Asp Gly Arg Asp Asp Glu Ala Lys Asp Glu Arg Ser Asp Met Tyr gaa tcg gac cgg aat gga cgc tgt tgc cat cct gcc tgt gcg aga aag
Glu Ser Asp Arg Asn Gly Arg Cys Cys His Pro Ala Cys Ala Arg Lys tat aat tgt gga cgc tgatgctcca ggaccctctg aaccacgacg t
Tyr Asn Cys Gly Arg
```

TABLE 29

DNA Sequence (SEQ ID NO:82) and Protein Sequence (SEQ ID NO:83) of O1.3

```
tctgatggca gggatgacac agccaaaaac aaaggatctg acatgaacaa attg gtc
                                                            Val aag aaa aaa caa tgt tgc aat cct gcc tgt ggc cca aag tat agt tgt
Lys Lys Lys Gln Cys Cys Asn Pro Ala Cys Gly Pro Lys Tyr Ser Cys gga cac tgatgctcca ggaccctctg aaccacgacg t
Gly His
```

TABLE 30

DNA Sequence (SEQ ID NO:84) and Protein Sequence (SEQ ID NO:85) of S1.3

```
tct gat ggc agg gat gac gaa gcc aaa gac gaa agg tct gac atg cac
Ser Asp Gly Arg Asp Asp Glu Ala Lys Asp Glu Arg Ser Asp Mer His
gaa tcg gac cgg aaa gga cgc gca tac tgt tgc cat cct gcc tgt ggc
Glu Ser Asp Arg Lys Gly Arg Ala Tyr Cys Cys His Pro Ala Cys Gly
aaa aag tat aat tgt gga cgc tgatgctcca ggaccctctg aaccacgacg t
Lys Lys Tyr Asn Cys Gly Arg
```

TABLE 31

DNA Sequence (SEQ ID NO:86) and Protein Sequence (SEQ ID NO:87) of EI

```
atg ttc acc gtg ttt ctg ttg gtt gtc ttg gca acc
Met Phe Thr Val Phe Leu Leu Val Val Leu Ala Thr act gtc ggt tcc ttc act tta gat cgt gca tct gat
Thr Val Gly Ser Phe Thr Leu Asp Arg Ala Ser Asp ggt agg gat gcc gca gcc aac gac aaa gcg tct gac
```

TABLE 31-continued

DNA Sequence (SEQ ID NO:86) and Protein Sequence (SEQ ID NO:87) of EI

```
Gly Arg Asp Ala Ala Ala Asn Asp Lys Ala Ser Asp ctg atc gct ctg acc gcc agg aga gat cca tgc tgt
Leu Ile Ala Leu Thr Ala Arg Arq Asp Prc Cys Cys tac cat cct acc tgt aac atg agt aat cca cag att
Tyr His Pro Thr Cys Asn Met Ser Asn Pro Gln Ile
```

TABLE 31-continued

DNA Sequence (SEQ ID NO:86) and Protein Sequence (SEQ ID NO:87) of EI tgt ggt
Cys Gly tgaagacgct gatgctccag gaccctctga accacgacgt

TABLE 32

DNA Sequence (SEQ ID NO:88) and Protein Sequence (SEQ ID NO:89) of EIA atg ttc acc gtg ttt ctg ttg gtt gtc ttg gca acc
Met Phe Thr Val Phe Leu Leu Val Val Leu Ala Thr act gtc ggt tcc ttc act tta gat cgt gca tct gat
Thr Val Gly Ser Phe Thr Leu Asp Arg Ala Ser Asp ggt agg gat gcc gca gcc aac gac aaa gcg tct gac
Gly Arg Asp Ala Ala Ala Asn Asp Lys Ala Ser Asp ctg atc gct ctg acc gcc agg aga gat cca tgc tgt
Leu Ile Ala Leu Thr Ala Arg Arg Asp Pro Cys Cys tcc aat cct gcc tgt aac gtg aat aat cca cag att
Ser Asn Pro Ala Cys Asn Val Asn Asn Pro Gln Ile tgt ggt
Cys Gly tgaagacgct gatgctccag gaccctctga accacgacgt

TABLE 33

DNA Sequence (SEQ ID NO:90) and Protein Sequence (SEQ ID NO:91) of P1.2 atg ttc acc gtg ttt ctg ttg gtg gat gcc gca gcc aac gac aag gcg
Met Phe Thr Val Phe Leu Leu Val Asp Ala Ala Ala Asn Asp Lys Ala tct gac cgg atc gct ctg acc gcc agg aga gat cca tgc tgt tcc aat
Ser Asp Arg Ile Ala Leu Thr Ala Arg Arg Asp Pro Cys Cys Ser Asn cct gtc tgt acc gtg cat aat cca cag att tgt ggt tgaagacgct
Pro Val Cys Thr Val His Asn Pra Gln Ile Cys Gly gatgctccag gaccctctga accacgacgt

TABLE 34

DNA Sequence (SEQ ID NO:92) and Protein Sequence (SEQ ID NO:93) of P1.3 atg ttc acc gtg ttt ctg ttg gtt gtc ttg gta acc
Met Phe Thr Val Phe Leu Leu Val Val Leu Val Thr acc gtc gtt tcc ttc aat tca gat cgt gca tta ggt
Thr Val Val Ser Phe Asn Ser Asp Arg Ala Leu Gly ggc agg aat gct gca gcc aaa gcg tct gac aag atc
Gly Arg Asn Ala Ala Ala Lys Ala Ser Asp tys Ile gct tcg atc ctc ggg aga aga gca tgc tgt tct tat
Ala Ser Ile Leu Gly Arg Arg Ala Cys Cys Ser Tyr cct ccc tgt aac gtg aac tat cca gaa att tgt ggt
Pro Pro Cys Asn Val Asn Tyr Pro Glu Ile Cys Gly gga cga ggc
Gly Arg Gly tgatgctcca ggaccctcrg aaccacgacg t

TABLE 35

DNA Sequence (SEQ ID NO:94) and Protein Sequence (SEQ ID NO:95) of Sl1.4

```
atg ttc acc gtg ttt ctg ttg gtt gtc ttg gca acc acc gtc gtt ccc
Met Phe Thr Val Phe Leu Leu Val Val Leu Ala Thr Thr Val Val Pro ttc aar tca gat cgt gat cca gca tta ggt ggc agg aat gct gca gcc
Phe Asn Ser Asp Arg Asp Pro Ala Leu Gly Gly Arg Asn Ala Ala Ala ata gcg tct gac aag atc gct tcg acc ctc agg aga gga gga tgc tgt
Ile Ala Ser Asp Lys Ile Ala Ser Thr Leu Arg Arg Gly Gly Cys Cys tct tat cct ccc tgt aac gtg tcc tat cca gaa att tgt ggt gga cga
Ser Tyr Pro Pro Cys Asn Val Ser Tyr Pro Glu Ile Cys Gly Gly Arg cgc tgatgctcca ggaccctctg aaccacgacgt
Arg
```

TABLE 36

DNA Sequence (SEQ ID NO:96) and Protein Sequence (SEQ ID NO:97) of Sl1.4A

```
atg ttc acc gtg ttt ctg ttg gtt gtc ttg gca acc
Met Phe Thr Val Phe Leu Leu VaL Val Leu Ala Thr acc gtc gtt tcc ttc aat tca gat cgt gca tta ggt
Thr Val Val Ser Phe Asn Ser Asp Arg Ala Leu Gly ggc agg aat gct gca gcc aaa gcg tct gac aag atc
Gly Arg Asn Ala Ala Ala Lys Ala Ser Asp Lys Ile gct tcg atc ctc ggg aga aga aga tgc tgt tct tat
Ala Ser Ile Leu Gly Arg Arg Arg Cys Cys Ser Tyr cct ccc tgt aac gtg tcc tat cca gaa att tgt ggt
Pro Pro Cys Asn Val Ser Tyr Pro Glu Ile Cys Gly gga cga cgc
Gly Arg Arg tgatgctcca ggaccctctg aaccacgacg t
```

TABLE 37

DNA Sequence (SEQ ID NO:98) and Protein Sequence (SEQ ID NO:99) of Sl1.8

```
atg ttc acc gtg ttt ctg ttg gtt gtc ttg gca acc
Met Phe Thr Val Phe Leu Leu Val Val Leu Ala Thr acc gtc gtt tcc ttc aat tca gat cgt gca tta ggt
Thr Val Val Ser Phe Asn Ser Asp Arg Ala Leu Gly ggc agg aat gct gca gcc aaa gcg tct gac aag atc
Gly Arg Asn Ala Ala Ala Lys Ala Ser Asp Lys Ile gct tcg atc ctc ggg aga aga gca tgc tgt tct tat
Ala Ser Ile Leu Gly Arg Arg Ala Cys Cys Ser Tyr cct ccc tgt aac gtg aac tat cca gaa att tgt ggt
Pro Pro Cys Asn Val Asn Tyr Pro Glu Ile Cys Gly gga cga ggc
Gly Arg Gly tgatgctcca ggaccctctg aaccacgacg t
```

TABLE 38

DNA Sequence (SEQ ID NO:100) and Protein Sequence (SEQ ID NO:101) of P1.1

```
atg ttc acc gtg ttt ctg ttg gtt gtc ttg gca acc
Met Phe Thr Val Phe Leu Leu Val Val Leu Ala Thr act gtc ggt tcc ttc act tta gat cgt gca tct gat
Thr Val Gly Ser Phe Thr Leu Asp Arg Ala Ser Asp ggt agg gar gcc gca gcc aac gac aaa gcg act gac
Gly Arg Asp Ala Ala Ala Asn Asp Lys Ala Thr Asp ctg atc gct ctg acc gcc agg aga gat cca tgc tgt
Leu Ile Ala Leu Thr Ala Arg Arg Asp Pro Cys Cys tcc aat ccr gtc tgt acc gtg cat aat cca cag att
Ser Asn Pro Val Cys Thr Val His Asn Pro Gln Ile tgt ggt
Cys Gly tgaagacgct gatgcttcag gaccctctga accacgacgt
```

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Blount, K. et al. (1992). *Toxicon* 30:835–842.
Bodansky et al. (1966). *Chem. Ind.* 38:1597–98.
Cruz, L. J. et al. (1987). *J. Biol. Chem.* 260:9280–9288.
Goodman and Gilman's *The Pharmacological Basis of Therapeutics*, 7th Ed., Section II (1985).
Gray, W. R. et al. (1981). *J. Biol. Chem.* 256:4734–4740.
Haack, J. A. et al. (1990). *J. Biol. Chem.* 265:6025–6029.
Horiki, K. et al. (1978). *Chemistry Letters* 165–68.
Kapoor (1970). *J. Pharm. Sci.* 59:1–27.
Kornreich, W. D. et al. (1986). U.S. Pat. No. 4,569,967.
Marshall, I. G. and Harvey, A. L. (1990). *Toxicon* 28:231–234.
McIntosh, J. M. et al. (1982). *Arch. Biochem. Biophys.* 218:329–334.
Mena, E. E. et al. (1990). *Neurosci. Lett.* 118:241–244.
*Methoden der Organischen Chemie* (Houben-Weyl): *Synthese von Peptiden*, E. Wunsch (Ed.), Georg Thieme Verlag, Stuttgart, Ger. (1974).

Myers, R. A. et al. (1991). *Biochemistry* 30:9370–9377.
Nishiuchi, Y. et al. (1993). *Int. J. Pept. Protein Res.* 42:533–538.
Nowak, L. et al. (1984). *Nature* 307:462–465.
Olivera, B. M. et al. (1984). U.S. Pat. No. 4,447,356.
Olivera, B. M. et al. (1985). *Science* 230:1338–1343.
Olivera, B. M. et al. (1996). U.S. Pat. No. 5,514,774.
*Physicians' Desk Reference*, 48th Ed., pp. 689,758,1362, 1648 (1994).
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual*, 2nd Ed., Cold Spring Harbor Laboratory, Cold Spring Harbor, N.Y.
Schroder & Lubke (1965). *The Peptides* 1:72–75, Academic Press, NY.
Stewart and Young, *Solid-Phase Peptide Synthesis*, Freeman & Co., San Francisco, Calif. (1969).
Vale et al. (1978). U.S. Pat. No. 4,105,603.
Zafaralla, G. C. et al. (1988). *Biochemistry* 27:7102–7105.
Zhou L. M., et al. (1996). *J. Neurochem,.* 66:620–628.
U.S. Pat. No. 3,972,859.
U.S. Pat. No. 3,842,067.
U.S. Pat. No. 3,862,925.
U.S. Pat. No. 4,190,674.
U.S. Pat. No. 4,179,507.
U.S. Pat. No. 4,508,715.
U.S. Pat. No. 4,701,460.
U.S. Pat. No. 4,761,418.
U.S. Pat. No. 4,923,898.
U.S. Pat. No. 5,015,741.
U.S. Pat. No. 5,260,337.

What is claimed is:

1. A substantially pure α-conotoxin peptide seleceted from the group consisting of:
   $Xaa_1$-Cys-Cys-Asn-$Xaa_2$-Ala-Cys-Gly-Arg-His-$Xaa_3$-Ser-Cys-$Xaa_4$-Gly (SEQ ID NO:3);
   Asn-Gly-Arg-Cys-Cys-His-$Xaa_2$-Ala-Cys-Gly-$Xaa_4$-His-Phe-Ser-Cys (SEQ ID NO:4);
   Gly-Arg-Gly-Arg-Cys-Cys-His-$Xaa_2$-Ala-Cys-Gly-$Xaa_2$-Asn-$Xaa_3$-Ser-Cys (SEQ ID NO:5);
   Cys-Cys-His-$Xaa_2$-Ala-Cys-Gly-Arg-$Xaa_4$-$Xaa_3$-Asn-Cys (SEQ ID NO:6);
   Cys-Cys-Cys-Asn-$Xaa_2$-Ala-Cys-Gly-$Xaa_2$-Asn-$Xaa_3$-Gly-Cys-Gly-Thr-Ser-Cys-Ser-Arg-$Xaa_2$-Ser-$Xaa_1$-$Xaa_2$-Arg-Arg (SEQ ID NO:7);
   Asn-Gly-His-Cys-Cys-His-$Xaa_2$-Ala-Cys-Gly-Gly-$Xaa_4$-$Xaa_3$-Val-$Xaa_4$-Cys (SEQ ID NO:8);
   Asn-Gly-Arg-Cys-Cys-His-$Xaa_2$-Ala-Cys-Gly-Gly-$Xaa_4$-$Xaa_3$-Val-$Xaa_4$-Cys (SEQ ID NO:9);
   Asn-Gly-Arg-Cys-Cys-His-$Xaa_2$-Ala-Cys-Gly-$Xaa_4$-His-Phe-Ile-Cys (SEQ ID NO:10);
   Asn-Gly-Arg-Cys-Cys-His-$Xaa_2$-Ala-Cys-Gly-$Xaa_4$-His-Phe-Ser-Cys (SEQ ID NO:11);
   Asn-Gly-Arg-Cys-Cys-His-$Xaa_2$-Ser-Cys-Gly-Arg-$Xaa_4$-$Xaa_3$-Asn-Cys (SEQ ID NO:12);
   Asn-Gly-Arg-Cys-Cys-His-$Xaa_2$-Ala-Cys-Ala-Arg-$Xaa_4$-$Xaa_3$-Asn-Cys (SEQ ID NO:13);
   Asn-$Xaa_1$-Arg-Cys-Cys-His-$Xaa_2$-Ala-Cys-Ala-Arg-$Xaa_4$-$Xaa_3$-Asn-Cys (SEQ ID NO:14);
   Asp-Gly-Arg-Cys-Cys-His-$Xaa_2$-Ala-Cys-Gly-Gln-Asn-$Xaa_3$-Ser-Cys (SEQ ID NO:15);
   Asp-Gly-Arg-Cys-Cys-His-$Xaa_2$-Ala-Cys-Ala-$Xaa_4$-His-Phe-Asn-Cys (SEQ ID NO:16);
   Asn-Gly-Arg-Cys-Cys-His-$Xaa_2$-Ala-Cys-Ala-$Xaa_4$-Asn-$Xaa_3$-Ser-Cys (SEQ ID NO:17);
   Asn-Gly-Arg-Cys-Cys-His-$Xaa_2$-Ala-Cys-Ala-Arg-$Xaa_4$-$Xaa_3$-Ser-Cys (SEQ ID NO:18);
   $Xaa_5$-Cys-Cys-Asn-$Xaa_2$-Ala-Cys-Gly-$Xaa_2$-$Xaa_4$-$Xaa_3$-Ser-Cys (SEQ ID NO:19);
   $Xaa_5$-Cys-Cys-His-$Xaa_2$-Ala-Cys-Gly-$Xaa_4$-$Xaa_4$-$Xaa_3$-Asn-Cys (SEQ ID NO:20);
   Ser-Gly-Arg-Cys-Cys-His-$Xaa_2$-Ala-Cys-Gly-Arg-$Xaa_4$-$Xaa_3$-Asn-Cys (SEQ ID NO:21);
   Arg-Asp-$Xaa_2$-Cys-Cys-Ser-Asn-$Xaa_2$-Val-Cys-Thr-Val-His-Asn-$Xaa_2$-Gln-Ile-Cys (SEQ ID NO:22);
   Arg-Ala-Cys-Cys-Ser-$Xaa_3$-$Xaa_2$-$Xaa_2$-Cys-Asn-Val-Asn-$Xaa_3$-$Xaa_2$-$Xaa_1$-Ile-Cys (SEQ ID NO:23);
   Gly-Gly-Cys-Cys-Ser-$Xaa_3$-$Xaa_2$-$Xaa_2$-Cys-Asn-Val-Ser-$Xaa_3$-$Xaa_2$-$Xaa_1$-Ile-Cys (SEQ ID NO:24);
   Ser-Leu-Leu-Cys-Cys-Thr-Ile-$Xaa_2$-Ser-Cys-$Xaa_4$-Ala-Ser-$Xaa_3$-$Xaa_2$-Asp-Ile-Cys (SEQ ID NO:27),
   wherein $Xaa_1$ is Glu or γ-carboxy-glutamate (Gla); $Xaa_2$ is Pro or hydroxy-Pro; $Xaa_3$ is Tyr, mono-halo-Tyr, di-halo-Tyr, O-sulpho-Tyr, O-phospho-Tyr or nitro-Tyr; $Xaa_4$ is Lys, N-methyl-Lys, N,N-dimethyl-Lys or N,N,N-trimethyl-Lys; $Xaa_5$ is Gln or pyro-Glu; and the C-terminus contains a carboxyl or amide group, the polypeptide being substantially free of other peptides.

2. The substantially pure α-conotoxin peptide of claim 1, wherein $Xaa_1$ is Glu.

3. The substantially pure α-conotoxin peptide of claim 1, wherein $Xaa_4$ is Lys.

4. The substantially pure α-conotoxin peptide of claim 1, wherein $Xaa_3$ is Tyr.

5. The substantially pure α-conotoxin peptide of claim 1, wherein $Xaa_3$ is mono-iodo-Tyr.

6. The substantially pure α-conotoxin peptide of claim 1, wherein $Xaa_3$ is di-iodo-Tyr.

7. The substantially pure α-conotoxin peptide of claim 1, wherein $Xaa_5$ is Gln.

8. The substantially pure α-conotoxin peptide of claim 1, which is modified to contain an O-glycan, an S-glycan or an N-glycan.

9. The substantially pure α-conotoxin peptide of claim 1, wherein said peptide has the amino acid sequence set forth in SEQ ID NO:3 and wherein $Xaa_1$ is Glu, $Xaa_2$ is Pro, $Xaa_3$ is Tyr and $Xaa_4$ is Lys.

10. The substantially pure α-conotoxin peptide of claim 1, wherein said peptide has the amino acid sequence set forth in SEQ ID NO:4 and wherein $Xaa_2$ is Pro and $Xaa_4$ is Lys.

11. The substantially pure α-conotoxin peptide of claim 1, wherein said peptide has the amino acid sequence set forth in SEQ ID NO:5 and wherein $Xaa_2$ is Pro and $Xaa_3$ is Tyr.

12. The substantially pure α-conotoxin peptide of claim 1, wherein said peptide has the amino acid sequence set forth in SEQ ID NO:6 and wherein $Xaa_2$ is Pro, $Xaa_3$ is Tyr and $Xaa_4$ is Lys.

13. The substantially pure α-conotoxin peptide of claim 1, wherein said peptide has the amino acid sequence set forth in SEQ ID NO:7 and wherein $Xaa_1$ is Glu, $Xaa_2$ is Pro and $Xaa_3$ is Tyr.

14. The substantially pure α-conotoxin peptide of claim 1, wherein said peptide has the amino acid sequence set forth in SEQ ID NO:8 and wherein $Xaa_2$ is Pro, $Xaa_3$ is Tyr and $Xaa_4$ is Lys.

15. The substantially pure α-conotoxin peptide of claim 1, wherein said peptide has the amino acid sequence set forth in SEQ ID NO:9 and wherein $Xaa_2$ is Pro, $Xaa_3$ is Tyr and $Xaa_4$ is Lys.

16. The substantially pure α-conotoxin peptide of claim 1, wherein said peptide has the amino acid sequence set forth in SEQ ID NO:10 and wherein $Xaa_2$ is Pro and $Xaa_4$ is Lys.

17. The substantially pure α-conotoxin peptide of claim 1, wherein said peptide has the amino acid sequence set forth in SEQ ID NO:11 and wherein $Xaa_2$ is Pro and $Xaa_4$ is Lys.

18. The substantially pure α-conotoxin peptide of claim 1, wherein said peptide has the amino acid sequence set forth in SEQ ID NO:12 and wherein $Xaa_2$ is Pro and $Xaa_4$ is Lys.

19. The substantially pure α-conotoxin peptide of claim 1, wherein said peptide has the amino acid sequence set forth in SEQ ID NO:13 and wherein $Xaa_2$ is Pro, $Xaa_3$ is Tyr and $Xaa_4$ is Lys.

20. The substantially pure α-conotoxin peptide of claim 1, wherein said peptide has the amino acid sequence set forth in SEQ ID NO:14 and wherein $Xaa_1$ is Glu, $Xaa_2$ is Pro, $Xaa_3$ is Tyr and $Xaa_4$ is Lys.

21. The substantially pure α-conotoxin peptide of claim 1, wherein said peptide has the amino acid sequence set forth in SEQ ID NO:15 and wherein $Xaa_2$ is Pro and $Xaa_3$ is Tyr.

22. The substantially pure α-conotoxin peptide of claim 1, wherein said peptide has the amino acid sequence set forth in SEQ ID NO:16 and wherein $Xaa_2$ is Pro and $Xaa_4$ is Lys.

23. The substantially pure α-conotoxin peptide of claim 1, wherein said peptide has the amino acid sequence set forth in SEQ ID NO:17 and wherein $Xaa_2$ is Pro, $Xaa_3$ is Tyr and $Xaa_4$ is Lys.

24. The substantially pure α-conotoxin peptide of claim 1, wherein said peptide has the amino acid sequence set forth in SEQ ID NO:18 and wherein $Xaa_2$ is Pro, $Xaa_3$ is Tyr and $Xaa_4$ is Lys.

25. The substantially pure α-conotoxin peptide of claim 1, wherein said peptide has the amino acid sequence set forth in SEQ ID NO:19 and wherein $Xaa_2$ is Pro, $Xaa_3$ is Tyr, $Xaa_4$ is Lys and $Xaa_5$ is Gln.

26. The substantially pure α-conotoxin peptide of claim 1, wherein said peptide has the amino acid sequence set forth in SEQ ID NO:20 and wherein $Xaa_2$ is Pro, $Xaa_3$ is Tyr, $Xaa_4$ is Lys and $Xaa_5$ is Gln.

27. The substantially pure α-conotoxin peptide of claim 1, wherein said peptide has the amino acid sequence set forth in SEQ ID NO:21 and wherein $Xaa_2$ is Pro, $Xaa_3$ is Tyr and $Xaa_4$ is Lys.

28. The substantially pure α-conotoxin peptide of claim 1, wherein said peptide has the amino acid sequence set forth in SEQ ID NO:22 and wherein $Xaa_2$ is Pro.

29. The substantially pure α-conotoxin peptide of claim 1, wherein said peptide has the amino acid sequence set forth in SEQ ID NO:23 and wherein $Xaa_1$ is Glu, $Xaa_2$ is Pro and $Xaa_3$ is Tyr.

30. The substantially pure α-conotoxin peptide of claim 1, wherein said peptide has the amino acid sequence set forth in SEQ ID NO:24 and wherein $Xaa_1$ is Glu, $Xaa_2$ is Pro and $Xaa_3$ is Tyr.

31. The substantially pure α-conotoxin peptide of claim 1, wherein said peptide has the amino acid sequence set forth in SEQ ID NO:25 and wherein $Xaa_1$ is Glu, $Xaa_2$ is Pro and $Xaa_3$ is Tyr.

32. The substantially pure α-conotoxin peptide of claim 1, wherein said peptide has the amino acid sequence set forth in SEQ ID NO:27 and wherein $Xaa_2$ is Pro, $Xaa_3$ is Tyr and $Xaa_4$ is Lys.

33. A substantially pure α-conotoxin protein precursor comprising an amino acid sequence selected from the group of amino acid sequences set forth in Tables 2–38.

* * * * *

UNITED STATES PATENT AND TRADEMARK OFFICE
CERTIFICATE OF CORRECTION

PATENT NO.  : 6,268,473 B1
DATED       : July 31, 2001
INVENTOR(S) : Baldomero M. Olivera et al.

It is certified that error appears in the above-identified patent and that said Letters Patent is hereby corrected as shown below:

Column 39,
Line 36, please correct claim 1 as shown below:

1. A substantially pure α-conotoxin peptide seleceted from the group consisting of:
   $Xaa_1$-Cys-Cys-Asn-$Xaa_2$-Ala-Cys-Gly-Arg-His-$Xaa_3$-Ser-Cys-$Xaa_4$-Gly (SEQ ID NO:3);
   Asn-Gly-Arg-Cys-Cys-His-$Xaa_2$-Ala-Cys-Gly-$Xaa_4$-His-Phe-Ser-Cys (SEQ ID NO:4);
   Gly-Arg-Gly-Arg-Cys-Cys-His-$Xaa_2$-Ala-Cys-Gly-$Xaa_2$-Asn-$Xaa_3$-Ser-Cys (SEQ ID NO:5);
   Cys-Cys-His-$Xaa_2$-Ala-Cys-Gly-Arg-$Xaa_4$-$Xaa_3$-Asn-Cys (SEQ ID NO:6);
   Cys-Cys-Cys-Asn-$Xaa_2$-Ala-Cys-Gly-$Xaa_2$-Asn-$Xaa_3$-Gly-Cys-Gly-Thr-Ser-Cys-Ser-Arg-$Xaa_2$-Ser-$Xaa_1$-$Xaa_2$-Arg-Arg (SEQ ID NO:7);
   Asn-Gly-His-Cys-Cys-His-$Xaa_2$-Ala-Cys-Gly-Gly-$Xaa_4$-$Xaa_3$-Val-$Xaa_4$-Cys (SEQ ID NO:8);
   Asn-Gly-Arg-Cys-Cys-His-$Xaa_2$-Ala-Cys-Gly-Gly-$Xaa_4$-$Xaa_3$-Val-$Xaa_4$-Cys (SEQ ID NO:9);
   Asn-Gly-Arg-Cys-Cys-His-$Xaa_2$-Ala-Cys-Gly-$Xaa_4$-His-Phe-Ile-Cys (SEQ ID NO:10);
   Asn-Gly-Arg-Cys-Cys-His-$Xaa_2$-Ala-Cys-Gly-$Xaa_4$-His-Phe-Ser-Cys (SEQ ID NO:11);
   Asn-Gly-Arg-Cys-Cys-His-$Xaa_2$-Ser-Cys-Gly-Arg-$Xaa_4$-$Xaa_3$-Asn-Cys (SEQ ID NO:12);
   Asn-Gly-Arg-Cys-Cys-His-$Xaa_2$-Ala-Cys-Ala-Arg-$Xaa_4$-$Xaa_3$-Asn-Cys (SEQ ID NO:13);
   Asn-$Xaa_1$-Arg-Cys-Cys-His-$Xaa_2$-Ala-Cys-Ala-Arg-$Xaa_4$-$Xaa_3$-Asn-Cys (SEQ ID NO:14);
   Asp-Gly-Arg-Cys-Cys-His-$Xaa_2$-Ala-Cys-Gly-Gln-Asn-$Xaa_3$-Ser-Cys (SEQ ID NO:15);
   Asp-Gly-Arg-Cys-Cys-His-$Xaa_2$-Ala-Cys-Ala-$Xaa_4$-His-Phe-Asn-Cys (SEQ ID NO:16);
   Asn-Gly-Arg-Cys-Cys-His-$Xaa_2$-Ala-Cys-Ala-$Xaa_4$-Asn-$Xaa_3$-Ser-Cys (SEQ ID NO:17);
   Asn-Gly-Arg-Cys-Cys-His-$Xaa_2$-Ala-Cys-Ala-Arg-$Xaa_4$-$Xaa_3$-Ser-Cys (SEQ ID NO:18);
   $Xaa_5$-Cys-Cys-Asn-$Xaa_2$-Ala-Cys-Gly-$Xaa_2$-$Xaa_4$-$Xaa_3$-Ser-Cys (SEQ ID NO:19);
   $Xaa_5$-Cys-Cys-His-$Xaa_2$-Ala-Cys-Gly-$Xaa_4$-$Xaa_4$-$Xaa_3$-Asn-Cys (SEQ ID NO:20);
   Ser-Gly-Arg-Cys-Cys-His-$Xaa_2$-Ala-Cys-Gly-Arg-$Xaa_4$-$Xaa_3$-Asn-Cys (SEQ ID NO:21);

UNITED STATES PATENT AND TRADEMARK OFFICE
CERTIFICATE OF CORRECTION

PATENT NO. : 6,268,473 B1
DATED : July 31, 2001
INVENTOR(S) : Baldomero M. Olivera et al.

It is certified that error appears in the above-identified patent and that said Letters Patent is hereby corrected as shown below:

Arg-Asp-$Xaa_2$-Cys-Cys-Ser-Asn-$Xaa_2$-Val-Cys-Thr-Val-His-Asn-$Xaa_2$-Gln-Ile-Cys (SEQ ID NO:22);

Arg-Ala-Cys-Cys-Ser-$Xaa_3$-$Xaa_2$-$Xaa_2$-Cys-Asn-Val-Asn-$Xaa_3$-$Xaa_2$-$Xaa_1$-Ile-Cys (SEQ ID NO:23);

Gly-Gly-Cys-Cys-Ser-$Xaa_3$-$Xaa_2$-$Xaa_2$-Cys-Asn-Val-Ser-$Xaa_3$-$Xaa_2$-$Xaa_1$-Ile-Cys (SEQ ID NO:24);

Cys-Cys-Ser-$Xaa_3$-$Xaa_2$-$Xaa_2$-Cys-Asn-Val-Ser-$Xaa_3$-$Xaa_2$-$Xaa_1$-Ile-Cys (SEQ ID NO:25),

Ser-Leu-Leu-Cys-Cys-Thr-Ile-$Xaa_2$-Ser-Cys-$Xaa_4$-Ala-Ser-$Xaa_3$-$Xaa_2$-Asp-Ile-Cys (SEQ ID NO:27), wherein $Xaa_1$ is Glu or γ-carboxy-glutamate (Gla); $Xaa_2$ is Pro or hydroxy-Pro; $Xaa_3$ is Tyr, mono-halo-Tyr, di-halo-Tyr, O-sulpho-Tyr, O-phospho-Tyr or nitro-Tyr; $Xaa_4$ is Lys, N-methyl-Lys, N,N-dimethyl-Lys or N,N,N-trimethyl-Lys; $Xaa_5$ is Gln or pyro-Glu; and the C-terminus contains a carboxyl or amide group, the polypeptide being substantially free of other peptides.

Signed and Sealed this

Twenty-third Day of March, 2004

JON W. DUDAS
*Acting Director of the United States Patent and Trademark Office*